United States Patent
Miyashita et al.

(10) Patent No.: US 10,873,032 B2
(45) Date of Patent: Dec. 22, 2020

(54) ORGANIC PHOTOELECTRIC CONVERSION ELEMENT, TWO-DIMENSIONAL SENSOR, IMAGE SENSOR, AND IMAGING APPARATUS

(71) Applicant: CANON KABUSHIKI KAISHA, Tokyo (JP)

(72) Inventors: Hirokazu Miyashita, Ebina (JP); Yosuke Nishide, Kawasaki (JP); Naoki Yamada, Inagi (JP); Jun Kamatani, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 134 days.

(21) Appl. No.: 16/114,686

(22) Filed: Aug. 28, 2018

(65) Prior Publication Data

US 2019/0013469 A1    Jan. 10, 2019

Related U.S. Application Data

(63) Continuation of application No. PCT/JP2017/001226, filed on Jan. 16, 2017.

(30) Foreign Application Priority Data

Mar. 3, 2016    (JP) ................................. 2016-040865

(51) Int. Cl.
| | | |
|---|---|---|
| *H01L 51/00* | (2006.01) | |
| *C07C 255/42* | (2006.01) | |
| *C07C 211/61* | (2006.01) | |
| *H04N 5/369* | (2011.01) | |
| *H01L 51/42* | (2006.01) | |
| *H01L 27/30* | (2006.01) | |

(52) U.S. Cl.
CPC .......... *H01L 51/006* (2013.01); *C07C 211/61* (2013.01); *C07C 255/42* (2013.01); *H01L 51/0046* (2013.01); *H01L 51/0061* (2013.01); *H01L 51/42* (2013.01); *H04N 5/379* (2018.08); *C07C 2602/08* (2017.05); *H01L 27/307* (2013.01); *H01L 51/0047* (2013.01); *H01L 51/0054* (2013.01); *H01L 51/0067* (2013.01); *H01L 51/0068* (2013.01); *H01L 51/0072* (2013.01); *H01L 51/0073* (2013.01); *H01L 51/0074* (2013.01); *Y02E 10/549* (2013.01)

(58) Field of Classification Search
CPC ............. H01L 51/006; H01L 51/0061; H01L 51/0046; H01L 51/42; H01L 51/0068; H01L 51/0073; H01L 51/0047; H01L 51/0067; H01L 51/0074; H01L 51/0072; H01L 27/307; H01L 51/0054; C07C 255/42; C07C 211/61; C07C 2602/08; Y02E 10/549; H04N 5/379

USPC ............................................. 136/263; 252/75
See application file for complete search history.

(56) References Cited

U.S. PATENT DOCUMENTS

| | | | |
|---|---|---|---|
| 6,583,557 B2 | 6/2003 | Hashimoto et al. | |
| 6,833,200 B2 | 12/2004 | Senoo et al. | |
| 8,338,691 B2 * | 12/2012 | Mitsui | B82Y 10/00 136/243 |
| 9,012,762 B2 | 4/2015 | Mitsui et al. | |
| 9,035,055 B2 * | 5/2015 | Hamano | C07C 223/06 546/61 |
| 2005/0025997 A1 | 2/2005 | Senoo et al. | |
| 2011/0056562 A1 * | 3/2011 | Hamano | C09B 23/04 136/263 |
| 2014/0151676 A1 * | 6/2014 | Klubek | H01L 51/0052 257/40 |
| 2020/0131103 A1 * | 4/2020 | Ohrui | C09K 11/06 |

FOREIGN PATENT DOCUMENTS

| | | |
|---|---|---|
| JP | 2010-103457 A | 5/2010 |
| JP | 2011-213706 A | 10/2011 |
| WO | 2017/149958 A1 | 9/2017 |
| WO | 2018/016354 A1 | 1/2018 |

OTHER PUBLICATIONS

Pyrene, Wikipedia (English), pp. 1-4, Jun. 10, 2020. (Year: 2020).*
Nishide et al., U.S. Appl. No. 16/106,534, filed Aug. 21, 2018.
Yamada et al., U.S. Appl. No. 16/051,724, filed Aug. 1, 2018.
International Preliminary Report on Patentability in International Application No. PCT/JP2017/001226 (dated Sep. 2018).
Yamada et al., U.S. Appl. No. 16/130,029, filed Sep. 13, 2018.
Lijun Zhu et al., "N-Annulated Perylene Dyes with Adjustable Photophysical Properties," 52(48) Tetrahedron Lett. 6411-6414 (Nov. 2011) (XP028331478).
International Search Report in International Application No. PCT/JP2017/001226 (dated Mar. 2017).

(Continued)

*Primary Examiner* — Douglas J McGinty
(74) *Attorney, Agent, or Firm* — Venable LLP

(57) ABSTRACT

Provided is an organic photoelectric conversion element including: an electron-collecting electrode; a hole-collecting electrode; and a photoelectric converter, which is arranged between the electron-collecting electrode and the hole-collecting electrode, wherein the photoelectric converter includes at least a first organic compound layer, and wherein the first organic compound layer contains a compound represented by the following general formula [1].

[1]

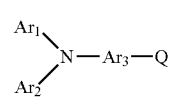

21 Claims, 5 Drawing Sheets

(56) References Cited

OTHER PUBLICATIONS

Nishide et al., U.S. Appl. No. 16/163,757, filed Oct. 18, 2018.
Yamada et al., U.S. Appl. No. 16/243,500, filed Jan. 9, 2019.

* cited by examiner

ORGANIC PHOTOELECTRIC CONVERSION ELEMENT, TWO-DIMENSIONAL SENSOR, IMAGE SENSOR, AND IMAGING APPARATUS

CROSS-REFERENCE TO RELATED APPLICATIONS

This application is a Continuation of International Patent Application No. PCT/JP2017/001226, filed Jan. 16, 2017, which claims the benefit of Japanese Patent Application No. 2016-040865, filed Mar. 3, 2016, both of which are hereby incorporated by reference herein in their entirety.

BACKGROUND OF THE INVENTION

Field of the Invention

The present invention relates to an organic photoelectric conversion element, and a two-dimensional sensor, an image sensor, and an imaging apparatus each using the organic photoelectric conversion element.

Description of the Related Art

A flat light-receiving element is widely used as an imaging element included in a camera or the like. The flat light-receiving element is an element in which a plurality of pixels each including a photodiode are two-dimensionally arrayed. In addition, when the flat light-receiving element receives light, signals (charges) generated by photoelectric conversion of the pixels are transferred using a CCD circuit or a CMOS circuit, and the signals are read out in the light-receiving element or in another member. In addition, as a photodiode included in a related-art imaging element, there is known one having a photoelectric converter formed in a semiconductor substrate made of silicon or the like.

Meanwhile, progress has been made in development of an element using an organic compound in its photoelectric converter, that is, an organic photoelectric conversion element. According to such organic photoelectric conversion element, in view of a high absorption coefficient and high flexibility of the organic compound, it is expected that the imaging element can be, for example, improved in sensitivity, thinned and reduced in weight, and made flexible. However, in general, a wavelength region of light to be absorbed by the organic compound is narrow, and the wavelength region of light to be absorbed by the organic compound depends in large part on a molecular size of the organic compound. Accordingly, few reports have been made on discovery and production of a compound having a low molecular weight and having an absorption spectrum in a long-wavelength region. Further, a wavelength region of light that can be subjected to photoelectric conversion with the organic photoelectric conversion element depends on the wavelength region of light to be absorbed by the organic compound serving as a constituent material for the photoelectric converter. Therefore, it is desired that an organic compound capable of absorbing all light in a visible light region be provided. In Japanese Patent Application Laid-Open No. 2010-103457, there is disclosed an organic photoelectric conversion element containing any one of the following Compounds 1-A to 1-C.

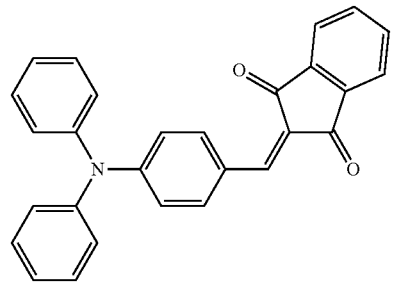

1-A

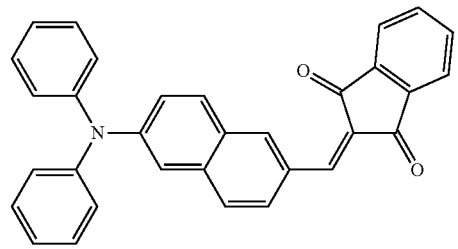

1-B

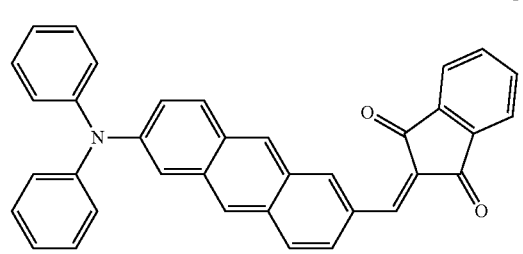 [SMILES: O=C1C(=Cc2ccc3cc4cc(N(c5ccccc5)c5ccccc5)ccc4cc3c2)C(=O)c2ccccc21]

1-C

An absorption spectrum of each of Compounds 1-A and 1-B disclosed in Japanese Patent Application Laid-Open No. 2010-103457 has its maximum absorption wavelength in a blue (wavelength: around 450 nm) to green (wavelength: around 500 nm) region, and the absorption spectrum has a narrow half width. Accordingly, the organic photoelectric conversion element using any such compound has low photoelectric conversion efficiency particularly in a red region (wavelength: around 600 nm). In addition, Compound 1-C disclosed in Japanese Patent Application Laid-Open No. 2010-103457 has low stability of the compound itself, and hence there is a problem in that use of Compound 1-C as a constituent material for the organic photoelectric conversion element impairs stability of the element.

The present invention has been accomplished in order to solve the above-mentioned problems, and the present invention is directed to providing an organic photoelectric conversion element having satisfactory photoelectric conversion efficiency throughout the entire visible light region, and having high stability of the element itself.

SUMMARY OF THE INVENTION

According to one aspect of the present invention, there is provided an organic photoelectric conversion element including: an electron-collecting electrode; a hole-collecting electrode; and a photoelectric converter, which is arranged between the electron-collecting electrode and the hole-collecting electrode, wherein the photoelectric converter includes at least a first organic compound layer, and wherein the first organic compound layer contains a compound represented by the following general formula [1]:

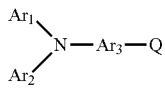

[1]

in the formula [1]: $Ar_1$ and $Ar_2$ each represent an alkyl group having 1 to 8 carbon atoms, an aromatic hydrocarbon group having 6 to 18 carbon atoms, or a heteroaromatic ring group having 3 to 15 carbon atoms, $Ar_1$ and $Ar_2$ may each further have a substituent selected from a halogen atom, a cyano group, an alkyl group having 1 to 6 carbon atoms, a phenyl group, a tolyl group, a xylyl group, a mesityl group, and a cumenyl group, and when $Ar_1$ and $Ar_2$ each represent an aromatic hydrocarbon group having 6 to 18 carbon atoms or a heteroaromatic ring group having 3 to 15 carbon atoms, $Ar_1$ and $Ar_2$ may be bonded to each other via any one of a single bond, and a methylene group and an ethylene group each of which may have an alkyl group to form a ring structure; $Ar_3$ represents a fused polycyclic aromatic hydrocarbon group formed by fusion of 4 or 5 six-membered rings, excluding an acene group, $Ar_3$ may further have a fluorine atom, a cyano group, a methyl group, or a tert-butyl group, and when $Ar_2$ represents an aromatic hydrocarbon group having 6 to 18 carbon atoms or a heteroaromatic ring group having 3 to 15 carbon atoms, $Ar_2$ and $Ar_3$ may be bonded to each other via any one of a single bond, and a methylene group and an ethylene group each of which may have an alkyl group to form a ring structure; and Q represents a substituent selected from a group of substituents represented by the following general formulae [2a] to [2e]:

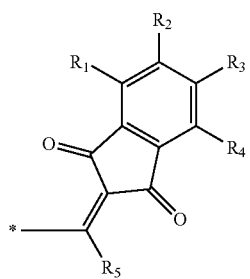

[2a]

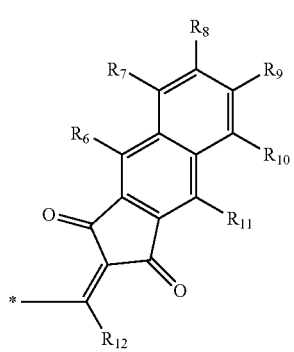

[2b]

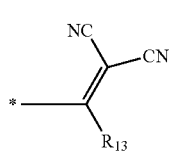

[2c]

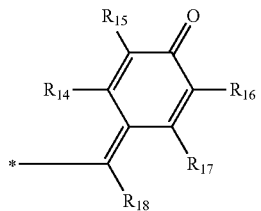

[2d]

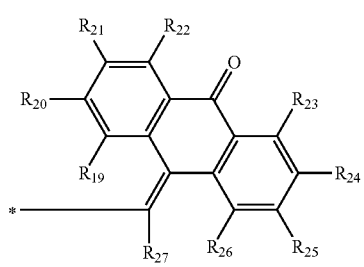

[2e]

in the formulae [2a] to [2e], $R_1$ to $R_{27}$ each represent a substituent selected from a hydrogen atom, a fluorine atom, an alkyl group having 1 to 4 carbon atoms, and a cyano group, and * represents a bonding site with $Ar_3$.

Further features of the present invention will become apparent from the following description of exemplary embodiments with reference to the attached drawings.

DESCRIPTION OF THE EMBODIMENTS

The present invention relates to an organic photoelectric conversion element including: an electron-collecting electrode; a hole-collecting electrode; and a photoelectric converter, which is arranged between the electron-collecting electrode and the hole-collecting electrode. In the present invention, the photoelectric converter includes at least a first organic compound layer, and the first organic compound layer contains a compound represented by the following general formula [1].

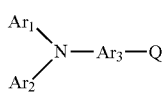

[1]

The details of the compound represented by the general formula [1] are described later.

Figure 1:
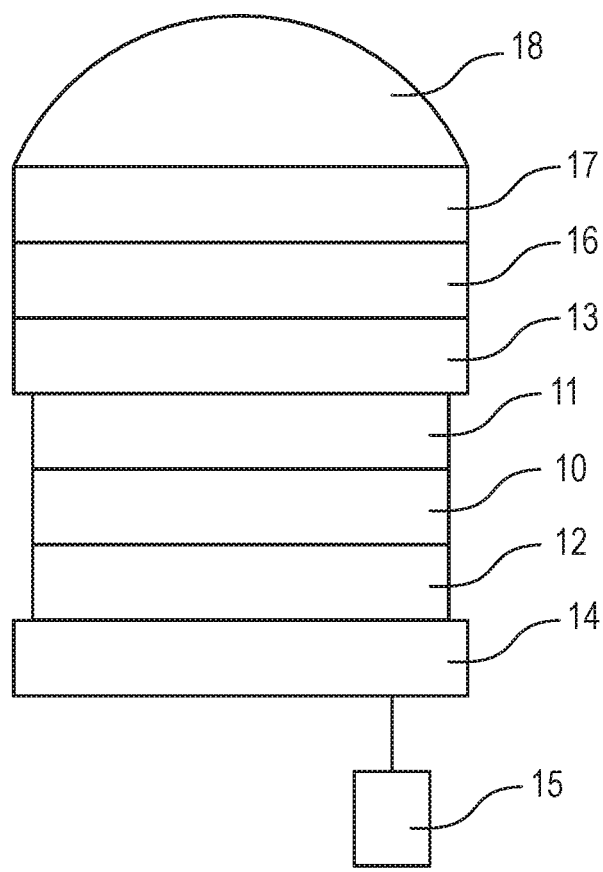
FIG. 1 is a cross-sectional schematic view for illustrating an example of an organic photoelectric conversion element according to an embodiment of the present invention.

1. Organic Photoelectric Conversion Element
(1) Organic Photoelectric Conversion Element According to Embodiment Now, an organic photoelectric conversion element according to an embodiment of the present invention is described with reference to the drawings. FIG. 1 is a cross-sectional schematic view for illustrating an example of the organic photoelectric conversion element according to the embodiment of the present invention. An organic photoelectric conversion element 1 illustrated in FIG. 1 includes a hole-collecting electrode 13, an electron-collecting electrode 14, and a first organic compound layer 10 arranged between the hole-collecting electrode 13 and the electron-collecting electrode 14.

The hole-collecting electrode 13 included in the organic photoelectric conversion element 1 illustrated in FIG. 1 is an electrode configured to collect a hole that is one of the charges generated in the first organic compound layer 10.

The electron-collecting electrode 14 included in the organic photoelectric conversion element 1 illustrated in FIG. 1 is, as described later, an electrode configured to collect an electron that is one of the charges generated in the first organic compound layer 10. In the organic photoelectric conversion element 1 illustrated in FIG. 1, the electron-collecting electrode 14 is arranged on a side closer to a pixel circuit (e.g., a readout circuit 15) with respect to the hole-collecting electrode 13. However, in the present invention, the hole-collecting electrode 13 may be arranged on the side closer to the pixel circuit with respect to the electron-collecting electrode 14.

In the organic photoelectric conversion element 1 illustrated in FIG. 1, the first organic compound layer 10 contains a compound to be excited when light is received in the layer. In addition, the first organic compound layer 10 plays a role also in transporting charges generated after the excitation of the molecule of the compound with light, namely an electron and a hole to the electron-collecting electrode 14 and the hole-collecting electrode 13, respectively. The first organic compound layer 10 contains an organic compound that converts light to charges as described later, and hence the first organic compound layer 10 is a photoelectric conversion layer or a layer included in a photoelectric converter. In the present invention, the photoelectric converter included in the organic photoelectric conversion element is not limited only to the first organic compound layer 10.

The first organic compound layer 10 is preferably a layer containing a p-type organic semiconductor or an n-type organic semiconductor. In addition, it is more preferred that at least part of the first organic compound layer 10 be a bulk heterojunction layer (mixed layer) containing the p-type organic semiconductor and the n-type organic semiconductor. When at least part of the first organic compound layer 10 is the bulk heterojunction layer containing the p-type organic semiconductor and the n-type organic semiconductor, the photoelectric conversion efficiency (sensitivity) of the element can be further improved. In addition, when the first organic compound layer 10 is formed so as to contain the p-type organic semiconductor and the n-type organic semiconductor at an appropriate mixing ratio, electron mobility and hole mobility in the first organic compound layer 10 can be enhanced, and hence the optical response speed of the organic photoelectric conversion element can be further increased.

In the present invention, the first organic compound layer 10 is preferably constituted of one layer, but may be constituted of a plurality of layers. In addition, in the present invention, the first organic compound layer 10 is preferably non-luminescent. As used herein, the term "non-luminescent" refers to a layer having a luminescence quantum efficiency of 1% or less, preferably 0.5% or less, more preferably 0.1% or less in a visible light region (wavelength: 400 nm to 730 nm). A case in which the first organic compound layer 10 serving as the photoelectric converter has a luminescence quantum efficiency of more than 1% is not preferred because sensing performance or imaging performance is affected when the organic photoelectric conversion element of the present invention is applied as a constituent member of a sensor or an imaging element. The details of compounds that may be contained in the first organic compound layer 10 are described later.

In the organic photoelectric conversion element 1 illustrated in FIG. 1, a second organic compound layer 11 is arranged between the hole-collecting electrode 13 and the first organic compound layer 10. In the present invention, the second organic compound layer 11 may be constituted of one layer, or may be constituted of a plurality of layers. In addition, the second organic compound layer 11 may be a bulk heterojunction layer (mixed layer) containing a plurality of kinds of materials. In the organic photoelectric conversion element 1 illustrated in FIG. 1, the second organic compound layer 11 plays a role in transporting a hole, which has migrated from the first organic compound layer 10, to the hole-collecting electrode 13. In addition, the second organic compound layer 11 suppresses the migration of an electron from the hole-collecting electrode 13 to the photoelectric converter. That is, the second organic compound layer 11 functions as a hole-transporting layer or an electron-blocking layer. As illustrated in FIG. 1, the second organic compound layer 11 is preferably brought into contact with the hole-collecting electrode 13.

In the present invention, as illustrated in FIG. 1, a third organic compound layer 12 may be arranged between the electron-collecting electrode 14 and the first organic compound layer 10. The third organic compound layer 12 is a layer to be arranged between the first organic compound layer 10 and the electron-collecting electrode 14. In the organic photoelectric conversion element 1 illustrated in FIG. 1, the third organic compound layer 12 plays a role in transporting an electron, which has migrated from the first organic compound layer 10, to the electron-collecting electrode 14. In addition, the third organic compound layer 12 is a layer for suppressing the flow of a hole from the electron-collecting electrode 14 into the first organic compound layer 10 (hole-blocking layer), and hence is preferably a layer having a high ionization potential. When the third organic compound layer 12 is arranged as illustrated in FIG. 1, the third organic compound layer 12 may be constituted of one layer, or may be constituted of a plurality of layers. In addition, the third organic compound layer 12 may be a bulk heterojunction layer (mixed layer) containing a plurality of kinds of materials. In addition, in the present invention, as illustrated in FIG. 1, the third organic compound layer 12 is arranged between the first organic compound layer 10 and the electron-collecting electrode 14. In this case, the third organic compound layer 12 is preferably brought into contact with the electron-collecting electrode 14.

In the present invention, layers to be arranged between the electron-collecting electrode 14 and the hole-collecting electrode 13 are not limited to the above-mentioned three kinds of layers (the first organic compound layer 10, the second organic compound layer 11, and the third organic compound layer 12). An interposing layer may be further arranged between the organic compound layers and the hole-collecting electrode 13, or between the organic compound layers and the electron-collecting electrode 14. The interposing layer is arranged for the purpose of improving charge injection efficiency in the injection of a generated charge into an electrode, or blocking a charge from being injected into the organic compound layer in the application of the charge. When the interposing layer is arranged, the interposing layer may be an organic compound layer containing an organic compound, or may be an inorganic compound layer containing an inorganic compound.

In the organic photoelectric conversion element 1 illustrated in FIG. 1, the electron-collecting electrode 14 is connected to the readout circuit 15. However, the readout circuit 15 may be connected to the hole-collecting electrode 13. The readout circuit 15 plays a role in reading out information based on a charge generated in the first organic compound layer 10, and transmitting the information to, for example, a signal processing circuit (not shown) arranged downstream. The readout circuit 15 includes, for example, a transistor configured to output a signal based on a charge generated in the organic photoelectric conversion element 1.

In the organic photoelectric conversion element 1 illustrated in FIG. 1, an inorganic protective layer 16 is arranged on the hole-collecting electrode 13. The inorganic protective layer 16 is a layer for protecting a member in which the electron-collecting electrode 14, the third organic compound layer 12, the first organic compound layer 10, the second organic compound layer 11, and the hole-collecting electrode 13 are laminated in the stated order. As a constituent material for the inorganic protective layer 16, there are given silicon oxide, silicon nitride, aluminum oxide, and the like, and the layer may be formed by a known film-forming method.

In the organic photoelectric conversion element 1 illustrated in FIG. 1, a color filter 17 is arranged on the inorganic protective layer 16. An example of the color filter 17 is a color filter configured to transmit red light in visible light. In addition, in the present invention, the color filter 17 may be arranged in such a manner that one color filter is arranged for each organic photoelectric conversion element, or in such a manner that one color filter is arranged for a plurality of organic photoelectric conversion elements. Further, when the color filters 17 are arrayed, for example, a Bayer array may be formed with adjacent organic photoelectric conversion elements.

In the organic photoelectric conversion element 1 illustrated in FIG. 1, an optical member, such as a microlens 18, is arranged on the color filter 17. The microlens 18 plays a role in concentrating incident light on the first organic compound layer 10 serving as the photoelectric converter. In addition, in the present invention, the microlens 18 may be arranged in such a manner that one microlens is arranged for each organic photoelectric conversion element, or in such a manner that one microlens is arranged for a plurality of organic photoelectric conversion elements. In the present invention, it is preferred that one microlens 18 be arranged for each organic photoelectric conversion element.

When photoelectric conversion is performed using the organic photoelectric conversion element according to the present invention, a voltage is preferably applied between the hole-collecting electrode 13 and the electron-collecting electrode 14. In this case, the voltage to be applied between the two electrodes, which may vary depending on the total thickness of the organic compound layers (10, 11, and 12), is preferably 1 V or more and 15 V or less, more preferably 2 V or more and 10 V or less.

(2) First Organic Compound Layer

Next, the first organic compound layer included in the photoelectric converter of the organic photoelectric conversion element according to the present invention is described in detail together with constituent materials contained in the layer.

(2-1) Compound of General Formula [1]

First, the compound of the following general formula [1] contained as one of the constituent materials in the first organic compound layer 10 is described.

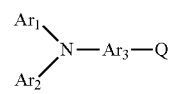

[1]

In the formula [1], $Ar_1$ and $Ar_2$ each independently represent an alkyl group having 1 to 8 carbon atoms, an aromatic hydrocarbon group having 6 to 18 carbon atoms, or a heteroaromatic ring group having 3 to 15 carbon atoms.

Examples of the alkyl group represented by each of $Ar_1$ and $Ar_2$ include a methyl group, an ethyl group, a n-propyl group, an iso-propyl group, a n-butyl group, an iso-butyl group, a sec-butyl group, a tert-butyl group, a n-pentyl group, a n-hexyl group, a cyclohexyl group, a n-heptyl group, and a n-octyl group. Of those, a methyl group and a tert-butyl group are preferred.

Examples of the aromatic hydrocarbon group represented by each of $Ar_1$ and $Ar_2$ include a phenyl group, a naphthyl group, a phenanthryl group, and a fluorenyl group. From the viewpoint of sublimability, a substituent having a relatively small molecular weight is preferred, and specifically, a phenyl group and a naphthyl group are preferred.

Examples of the heteroaromatic ring group represented by each of $Ar_1$ and $Ar_2$ include a pyridyl group, a pyrazinyl group, a pyrimidinyl group, a quinolyl group, an isoquinolyl group, a thienyl group, a furanyl group, a benzothienyl group, a benzofuranyl group, and a triazinyl group. From the viewpoints of sublimability and stability, a substituent having a relatively small molecular weight and having high stability is preferred, and specifically, a pyridyl group, a benzothienyl group, and a benzofuranyl group are preferred.

$Ar_1$ and $Ar_2$ may each further have a substituent selected from halogen atoms, such as a fluorine atom, a chlorine atom, a bromine atom, and an iodine atom, a cyano group, alkyl groups each having 1 to 6 carbon atoms, such as a methyl group, an ethyl group, a n-propyl group, an iso-propyl group, a n-butyl group, an iso-butyl group, a sec-butyl group, a tert-butyl group, a n-pentyl group, a n-hexyl group, and a cyclohexyl group, a phenyl group, a tolyl group, a xylyl group, a mesityl group, and a cumenyl group. When any one of $Ar_1$ and $Ar_2$ further has an alkyl group having 1 to 6 carbon atoms, a methyl group and a tert-butyl group are each preferred as the alkyl group. When any one of $Ar_1$ and $Ar_2$ further has a halogen atom, a fluorine atom is preferred as the halogen atom.

In addition, when $Ar_1$ and $Ar_2$ each represent an aromatic hydrocarbon group having 6 to 18 carbon atoms or a heteroaromatic ring group having 3 to 15 carbon atoms, $Ar_1$ and $Ar_2$ may be bonded to each other via any one of a single bond, and a methylene group and an ethylene group each of which may have an alkyl group, such as a methyl group, to form a ring structure, for example, any one of the following ring structures.

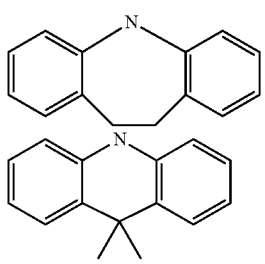

In the formula [1], $Ar_3$ represents a fused polycyclic aromatic hydrocarbon group formed by fusion of 4 or 5 six-membered rings. However, substituents belonging to acene groups, specifically, tetracenediyl groups and pentacenediyl groups are excluded. The reason why the acene groups are excluded from the substituent represented by $Ar_3$ in the present invention is described later.

The fused polycyclic aromatic hydrocarbon group represented by $Ar_3$ is preferably a substituent selected from a pyrenediyl group, a benzopyrenediyl group, a triphenylenediyl group, a perylenediyl group, and a chrysenediyl group. In consideration of the sublimability of the compound itself, the substituent serving as $Ar_3$ is more preferably a pyrenediyl group having a relatively small molecular weight. On one hand, in consideration of shifting of the absorption spectrum of the compound itself to longer wavelengths, the substituent serving as $Ar_3$ is more preferably a perylenediyl group. On the other hand, in consideration of the transition (dipole) moment of the compound itself, the substituent serving as $Ar_3$ is more preferably a pyrene-1,6-diyl group or a perylene-3,10-diyl group. This is because those substituents are each a substituent considered to facilitate the transition of an electron to increase an absorption coefficient among pyrenediyl groups and perylenediyl groups.

$Ar_3$ may further have a fluorine atom, a cyano group, a methyl group, or a tert-butyl group.

In addition, when $Ar_2$ represents an aromatic hydrocarbon group having 6 to 18 carbon atoms or a heteroaromatic ring group having 3 to 15 carbon atoms, $Ar_2$ and $Ar_3$ may be bonded to each other via any one of a single bond, and a methylene group and an ethylene group each of which may have an alkyl group, such as a methyl group, to form a ring structure, for example, any one of the following ring structures.

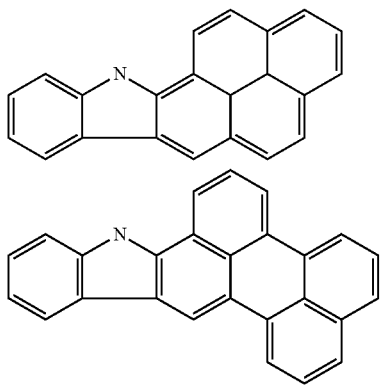

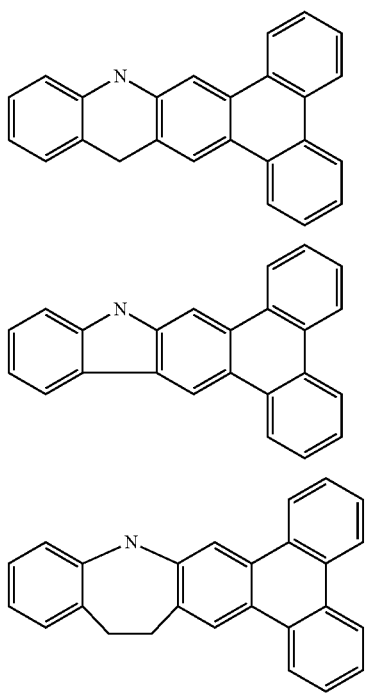

In the formula [1], Q represents a substituent selected from a group of substituents represented by the following general formulae [2a] to [2e]. In consideration of sublimability and stability, of the group of substituents represented by the formulae [2a] to [2e], a group of substituents represented by the formulae [2a] to [2c], each of which is a substituent having a relatively small molecular weight and having high stability, are preferred. A substituent represented by the formula [2a] or [2c] is more preferred.

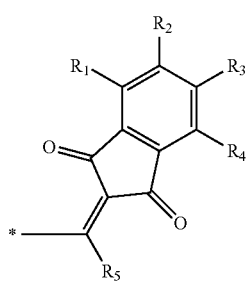

[2a]

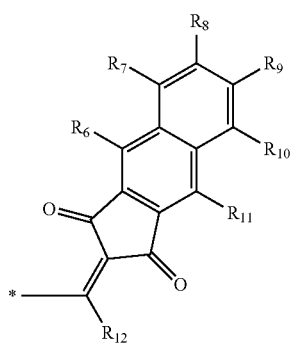

[2b]

-continued

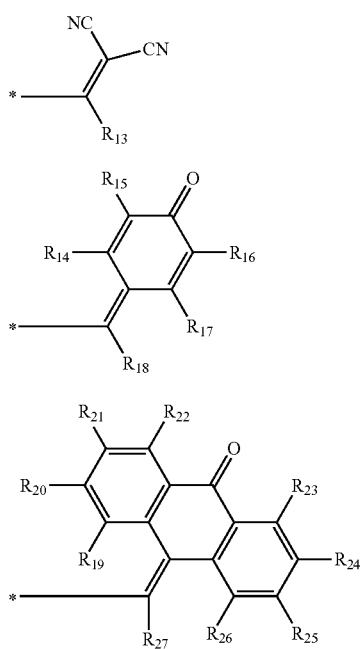

In the formulae [2a] to [2e], $R_1$ to $R_{27}$ each represent a substituent selected from a hydrogen atom, a fluorine atom, an alkyl group having 1 to 4 carbon atoms, and a cyano group.

Examples of the alkyl group represented by each of $R_1$ to $R_{27}$ include a methyl group, an ethyl group, an n-propyl group, an iso-propyl group, a n-butyl group, an iso-butyl group, a sec-butyl group, and a tert-butyl group. Of those substituents, a methyl group or a tert-butyl group is preferred.

In the formulae [2a] to [2e], * represents a bonding site with $Ar_3$.

(Synthesis Method for Compound of General Formula [1])

Next, a synthesis method for the compound of the general formula [1] is described. The compound of the general formula [1] may be synthesized, for example, in accordance with the synthesis scheme of the following formula [3].

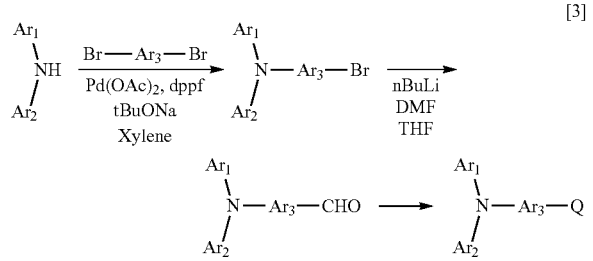

The synthesis scheme of the formula [3] is a synthesis scheme involving performing the following reactions [3a] to [3c] in this order.

[3a] A reaction for cross-coupling an aryl dihalide and an amine at 1:1 using a Pd catalyst

[3b] A reaction for formylating (ketonizing) a halide using n-butyllithium

[3c] Knoevenagel condensation

In addition, when $Ar_1$ and $Ar_2$, or $Ar_2$ and $Ar_3$ in the formula [1] are bonded to each other via a single bond, or a methylene group or an ethylene group (that may have an alkyl group) to form a ring structure, the compound may be synthesized, for example, in accordance with the synthesis scheme of the following formula [4].

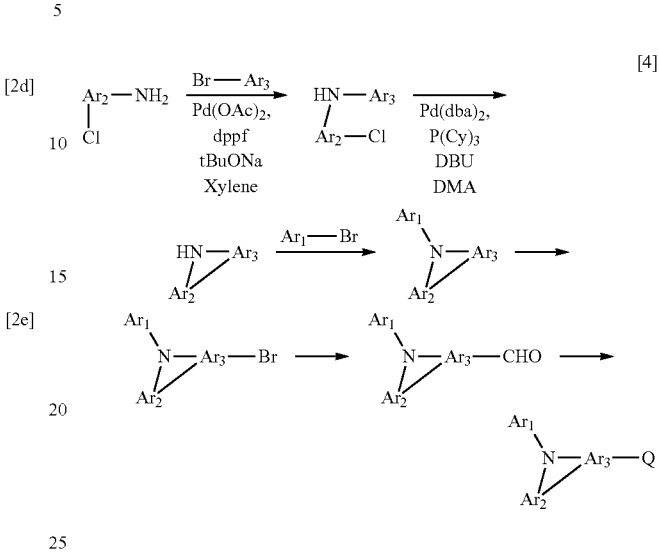

The synthesis scheme of the formula [4] is a synthesis scheme involving performing the following reactions [4a] to [4f] in this order.

[4a] A reaction for cross-coupling an aryl halide and an amine at 1:1 using a Pd catalyst

[4b] The formation of a ring structure by a Heck reaction

[4c] A reaction for cross-coupling an aryl halide and an amine having the ring structure formed in the [4b] using a Pd catalyst

[4d] A bromination reaction for the substituent serving as $Ar_3$ (including the case of being included in the ring structure formed in the [4b])

[4e] A reaction for formylating (ketonizing) a halide using n-butyllithium

[4f] Knoevenagel condensation

When, in the formula [4], the aryl halide to be used in the [4a] is $Ar_1$—Br, a compound having a ring structure in which $Ar_1$ and $Ar_2$ are bonded to each other via a single bond, or a methylene group or an ethylene group (that may have an alkyl group) is obtained.

(Properties of Compound of General Formula [1])

The compound of the general formula [1] has a structure in which a (hetero)arylamine site having a high electron-donating property, and a substituent having a high electron-accepting property are linked to each other via a divalent fused polycyclic aromatic hydrocarbon group ($Ar_3$). In the compound of the general formula [1], the substituent (linking group) linking the site having a high electron-donating property and the site having a high electron-accepting property to each other is a relatively large fused polycyclic aromatic hydrocarbon group. As a result, the compound of the general formula [1] has the following properties (i) and (ii).

(i) The half width of the absorption spectrum (width of a wavelength region in which a relative absorbance with respect to the maximum of absorption becomes 0.5 or more) is wide, and the maximum of absorption is present in a long-wavelength region. Accordingly, the compound has an absorption region throughout the entire visible light region.

(ii) The compound has no reaction active site on its structure, and has high stability of the compound itself.

Figure 2:
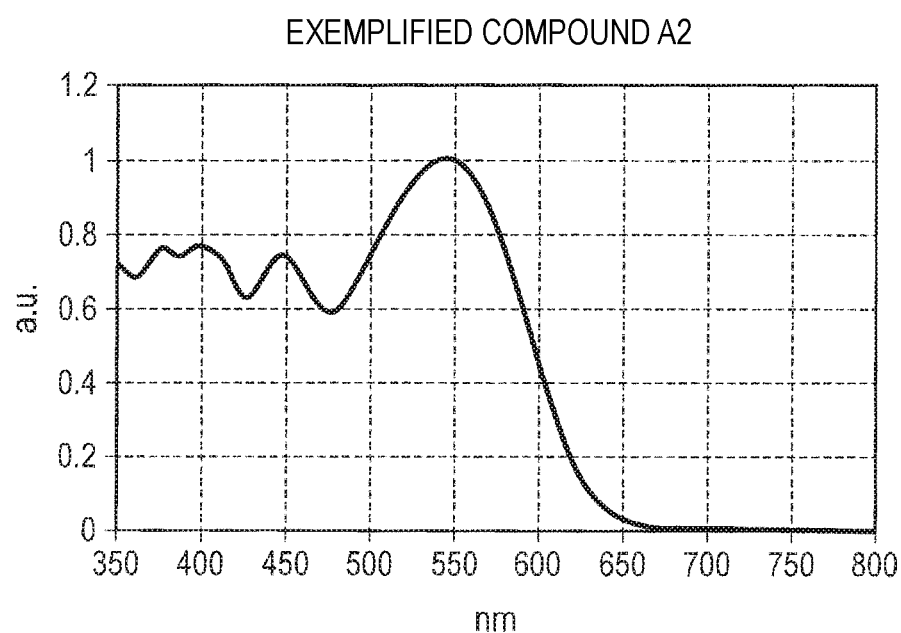
FIG. 2 is a graph for showing a UV-visible absorption spectrum of Exemplified Compound A2.
Figure 3:
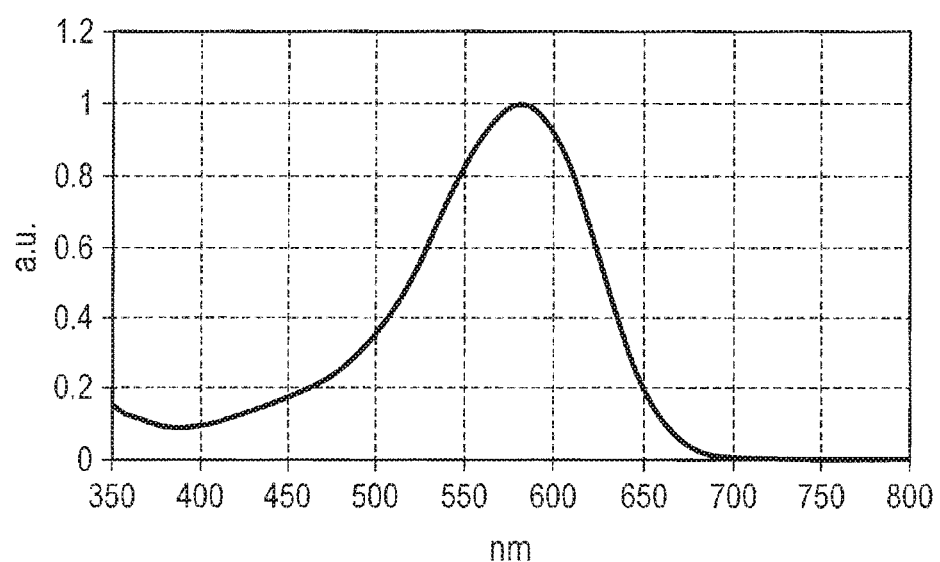
FIG. 3 is a graph for showing a UV-visible absorption spectrum of Exemplified Compound A19.

Now, UV-visible absorption spectra of compounds encompassed in the compound of the general formula [1] are measured, and general forms of the absorption spectra, in particular, the half widths of the absorption spectra and the positions of the maxima of absorption (maximum absorption wavelengths) are examined. FIG. 2 is a graph for showing a UV-visible absorption spectrum of Exemplified Compound A2 shown below. In addition, FIG. 3 is a graph for showing a UV-visible absorption spectrum of Exemplified Compound A19 shown below.

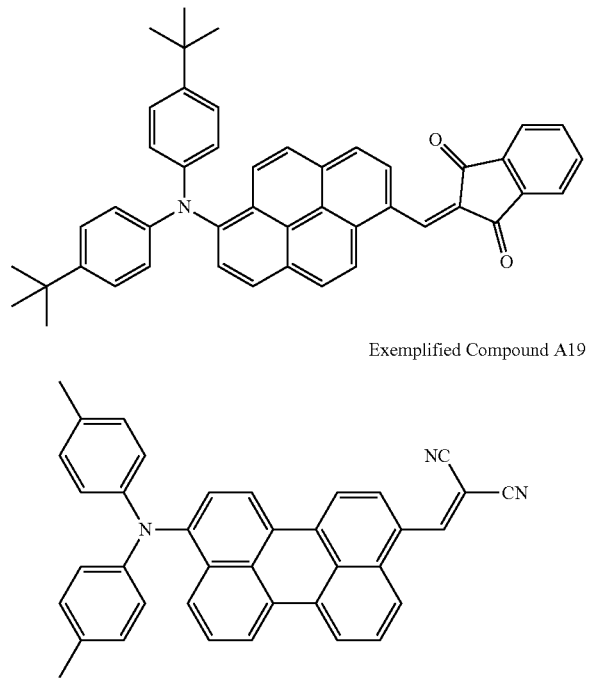

Exemplified Compound A2

Exemplified Compound A19

The measurement of the UV-visible absorption spectra was performed in a dilute toluene solution and under the condition of room temperature. In addition, Model V-560 (product name) manufactured by JASCO Corporation was used as a measurement apparatus. As a result of the measurement, it was found from FIG. 2 that Exemplified Compound A2 had a maximum absorption wavelength of 546 nm, and a half width in the visible light region of 198 nm (400 nm to 598 nm). In addition, it was found from FIG. 3 that Exemplified Compound A19 had a maximum absorption wavelength of 582 nm, and a half width in the visible light region of 112 nm.

The inventors of the present invention have also measured UV-visible absorption spectra of Comparative Compounds 1 and 2 shown below. Comparative Compound 1 is Compound 1-A disclosed in Japanese Patent Application Laid-Open No. 2010-103457, and Comparative Compound 2 is Compound 1-B disclosed in Japanese Patent Application Laid-Open No. 2010-103457.

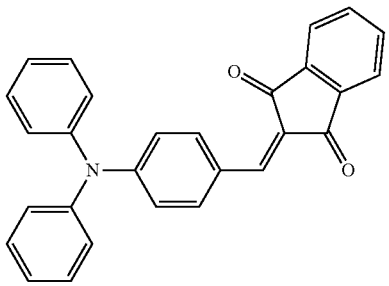

Comparative Compound 1

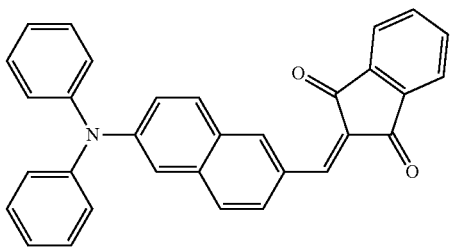

Comparative Compound 2

Figure 4:
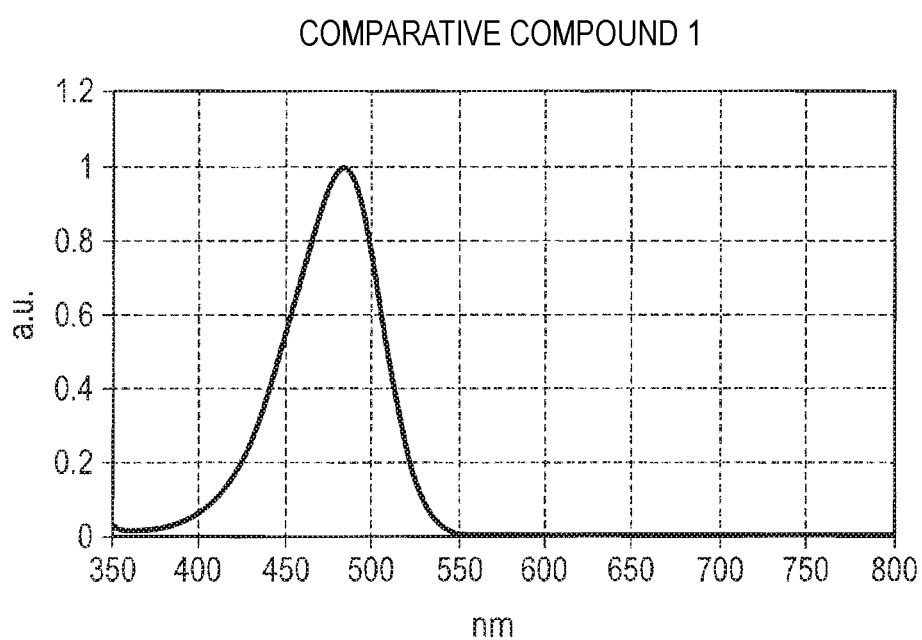
FIG. 4 is a graph for showing a UV-visible absorption spectrum of Comparative Compound 1.
Figure 5:
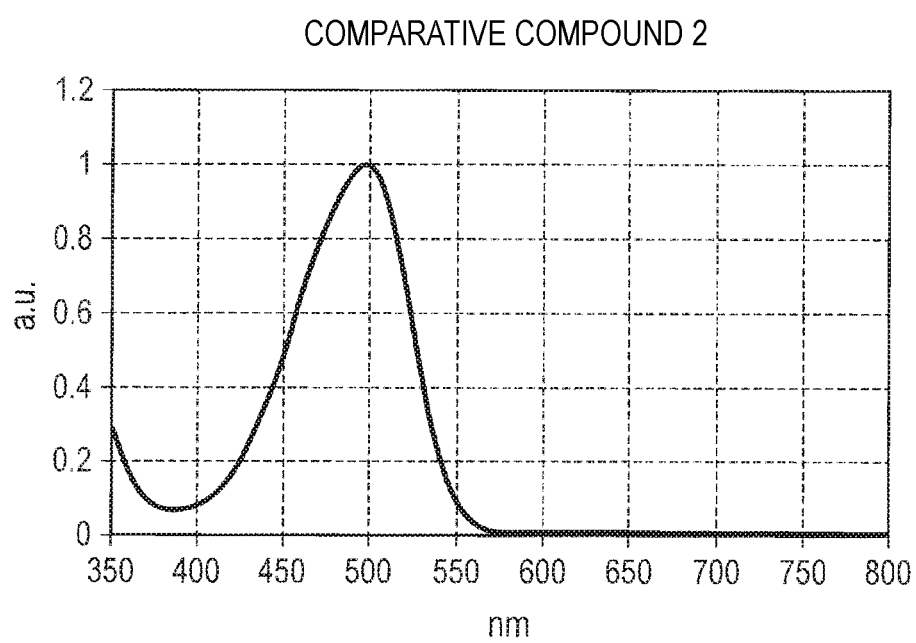
FIG. 5 is a graph for showing a UV-visible absorption spectrum of Comparative Compound 2.

FIG. 4 is a graph for showing the UV-visible absorption spectrum of Comparative Compound 1. In addition, FIG. 5 is a graph for showing the UV-visible absorption spectrum of Comparative Compound 2. Conditions for the measurement of the UV-visible absorption spectra are the same as those in the case of Exemplified Compound A2 and Exemplified Compound A19. As a result of the measurement, it was found from FIG. 4 that Comparative Compound 1 had a maximum absorption wavelength of 484 nm, and a half width in the visible light region of 62 nm. In addition, it was found from FIG. 5 that Comparative Compound 2 had a maximum absorption wavelength of 498 nm, and a half width in the visible light region of 76 nm.

The measurement results of the UV-visible absorption spectra of the compounds have shown that each of Comparative Compounds 1 and 2 has a narrow wavelength region of light to be absorbed by the compound itself, and in particular, has almost no absorption in a red region (around 600 nm). Therefore, Comparative Compounds 1 and 2 are not suited as constituent materials for an organic photoelectric conversion element. Meanwhile, each of the compounds encompassed in the compound of the general formula [1] (Exemplified Compound A2 and Exemplified Compound A19) has a wide absorption wavelength region of the compound itself, and shows a shift of the maximum absorption wavelength to longer wavelengths.

In this regard, a discussion is made as described below. That is, in the compound of the general formula [1], the electron-donating site and the electron-accepting site are linked to each other via a relatively large fused polycyclic aromatic hydrocarbon group. Accordingly, it is considered that absorption caused by charge-transfer (CT) transition between the electron-donating site and the electron-accepting site, and absorption caused by π-π* transition of the fused polycyclic aromatic hydrocarbon group linking those sites to each other coexist with each other. In this connection, the shift of the maximum absorption wavelength to longer wavelengths is considered to result from the CT transition via the fused polycyclic aromatic hydrocarbon group that is a linking group having a long conjugation length. In addition, the widening of the absorption spectrum (increase of the half width) is considered to result from the π-π* transition of the fused polycyclic aromatic hydrocarbon group linking the electron-donating site and the electron-accepting site to each other.

Next, it is described that the compound of the general formula [1] has no reaction active site, and has high stability of the compound itself. It is considered, from the foregoing description, that the stability of the compound of the general formula [1] itself is associated with the size of the fused polycyclic aromatic hydrocarbon group linking the electron-donating site and the electron-accepting site to each other, and the absorption spectrum of the compound. In view of the foregoing, an attempt was made to synthesize Comparative Compound 3 shown below, the compound containing an anthracene-2,6-diyl group (fused polycyclic aromatic hydrocarbon group) as the linking group. Comparative Compound 3 is Compound 1-C disclosed in Japanese Patent Application Laid-Open No. 2010-103457.

Comparative Compound 3

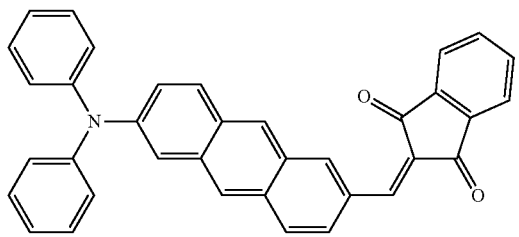

However, Comparative Compound 3 was found to be decomposed by oxidation during synthesis, and was not able to be synthesized. This is probably because Comparative Compound 3 has a reaction active site.

Incidentally, among fused polycyclic aromatic hydrocarbons, a compound having a structure in which a plurality of benzene rings are linearly fused is called an acene. As one of the features of an acene compound, it is known that its structure becomes more unstable as the number of benzene rings to be fused increases (to at least 3).

For example, anthracene, which is a typical acene compound shown below, receives electron donation from benzene rings at both ends, and hence has a high electron density at the central benzene ring. Accordingly, anthracene is liable to be subjected to an oxidation reaction at the central benzene ring. That is, anthracene has sites unstable against oxidation (active sites) at the 9-position and the 10-position in the center.

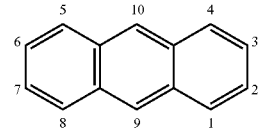

In this connection, the structures of Exemplified Compounds A2 and A19, and Comparative Compound 3 are shown in Table 1 below.

TABLE 1

| Compound | Presence or absence of active site in molecular structure |
|---|---|
| Comparative Compound 3 | ![structure] |
| Exemplified Compound A2 | ![structure] |

TABLE 1-continued

| Compound | Presence or absence of active site in molecular structure |
|---|---|
| Exemplified Compound A19 | 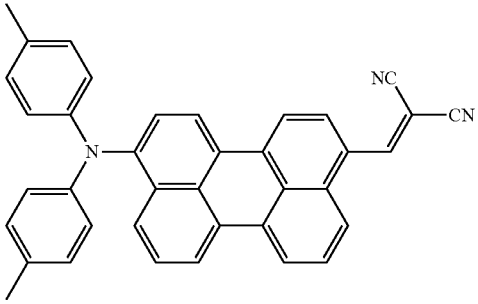 |

As shown in Table 1, Comparative Compound 3 has an anthracene skeleton, which is an acene, as a partial structure. In addition, in the anthracene skeleton, substitution positions (9-position and 10-position) each indicated by ★ in Table 1 serve as reaction active sites. Accordingly, Comparative Compound 3 is a compound unstable against oxidation, and hence is a material not suited as a constituent material for an organic photoelectric conversion element. Meanwhile, the compounds encompassed in the compound represented by the general formula [1] (Exemplified Compound A2 and Exemplified Compound A19) do not have a partial skeleton having a reaction active site, and hence are compounds stable against oxidation.

Accordingly, the compound of the general formula [1] is a compound having the properties (i) and (ii), and hence allows photoelectric conversion throughout the entire visible light region as compared to Comparative Compounds 1 to 3, and an organic photoelectric conversion element containing the compound of the general formula [1] has higher stability of the element itself.

In addition, when the compound of the general formula [1] is used as a constituent material for an organic photoelectric conversion element, a spin coating method may be adopted as a method of forming a layer containing the compound of the general formula [1] (first organic compound layer 10), but vapor deposition under a vacuum (vacuum deposition method) is preferably utilized. This is because the utilization of the vacuum deposition method allows the formation of a high-purity thin film. When the vacuum deposition method is utilized to form the first organic compound layer as described above, in general, as the molecular weight of the organic compound serving as the constituent material for the layer increases, a higher temperature is required. Besides, when the required temperature is too high, thermal decomposition of the organic compound serving as the constituent material, and the like are liable to occur. Therefore, in order that sublimation purification and film formation can be performed without excessive heating, a compound having a smaller molecular weight is preferably selected. In addition, the selection of a structure having no reaction active substitution position as a partial structure contained in the compound is preferred because the stability of the compound itself under high temperature is enhanced.

For example, when at least one of $Ar_1$ and $Ar_2$ in the formula [1] represents an aromatic hydrocarbon group, a phenyl group and a naphthyl group are each preferred because of being a substituent having a relatively small molecular weight. In addition, when at least one of $Ar_1$ and $Ar_2$ represents a heteroaromatic ring group, a pyridyl group, a benzothienyl group, and a benzofuranyl group are each preferred because of being a substituent having a relatively small molecular weight and high stability. Further, among substituents encompassed in Q in the formula [1], the substituents of the formulae [2a] to [2c] are each preferred because of being a substituent having a relatively small molecular weight and high stability.

In the organic photoelectric conversion element of the present invention, whether or not the compound of the general formula [1] is present in a constituent member of the organic photoelectric conversion element, such as the first organic compound layer 10, may be examined by analyzing the layer included in the organic photoelectric conversion element by TOF-SIMS or the like. In addition, instead of the analysis by TOF-SIMS or the like, there may be adopted a method involving extracting a constituent material for the organic photoelectric conversion element, followed by analysis by IR, UV, NMR, or the like.

(Specific Examples of Compound of General Formula [1])

Specific examples of the compound of the general formula [1] are shown below. However, in the present invention, the compound of the general formula [I] is not limited to these specific examples.

A1

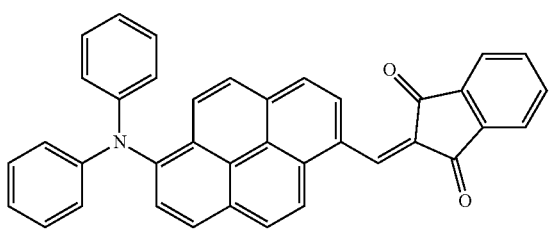

A2
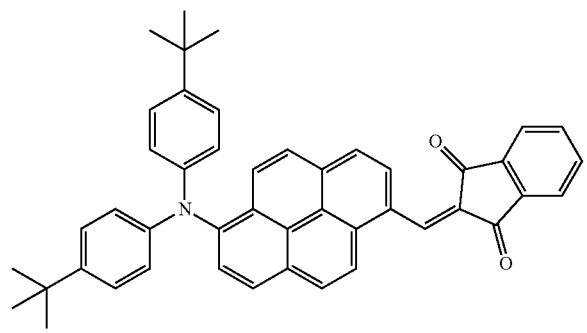 [SMILES: CC(C)(C)c1ccc(N(c2ccc(C(C)(C)C)cc2)c2ccc3ccc4c(C=C5C(=O)c6ccccc6C5=O)ccc5ccc2c3c54)cc1]
A3
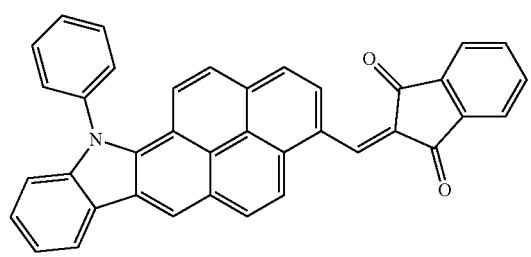
A4
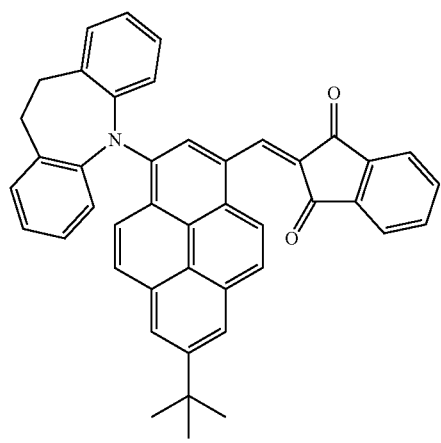
A5
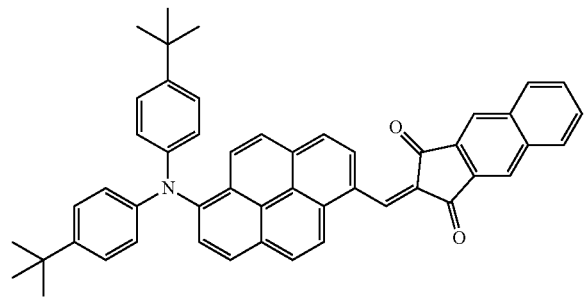
A6
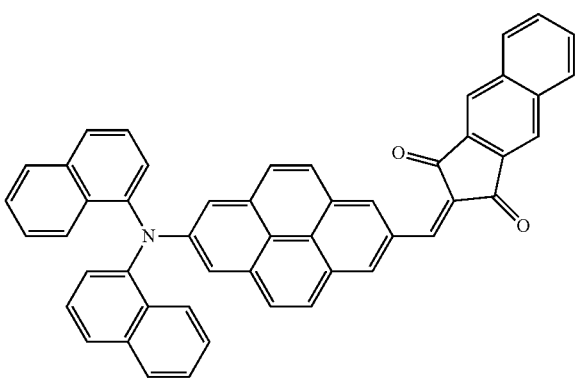
A7
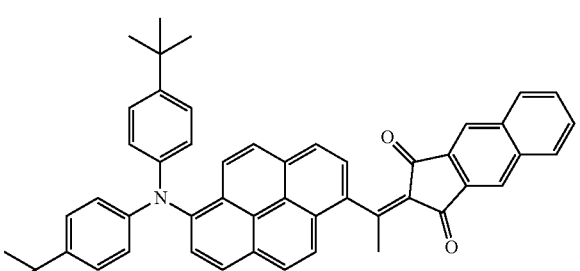
A8
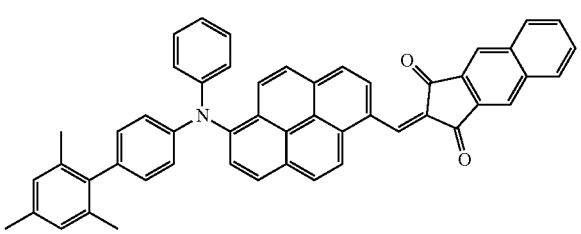
A9
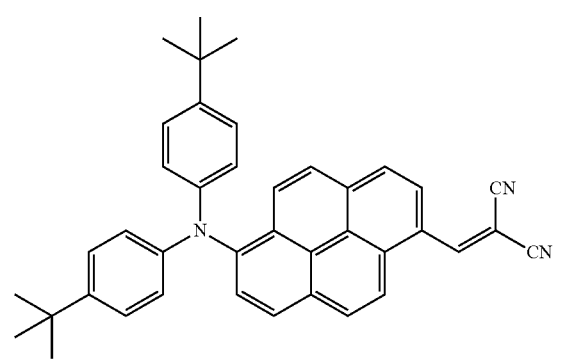

-continued
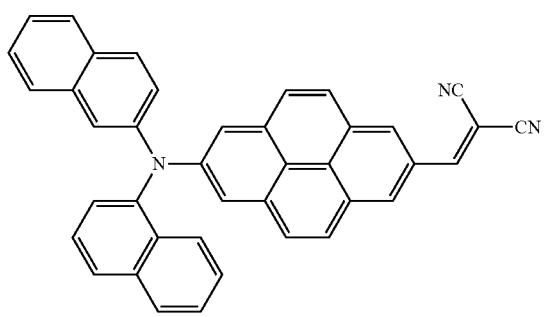
A10
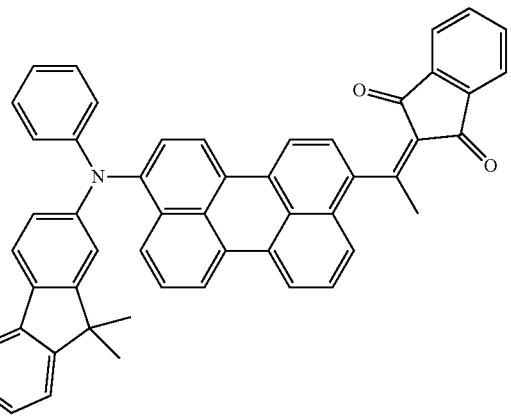
A14
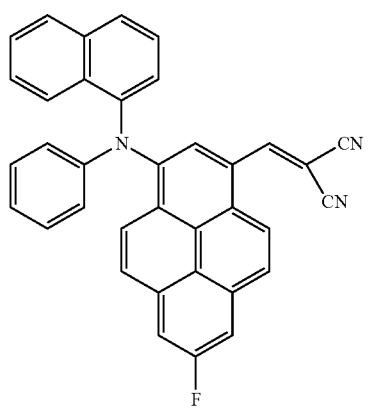
A11
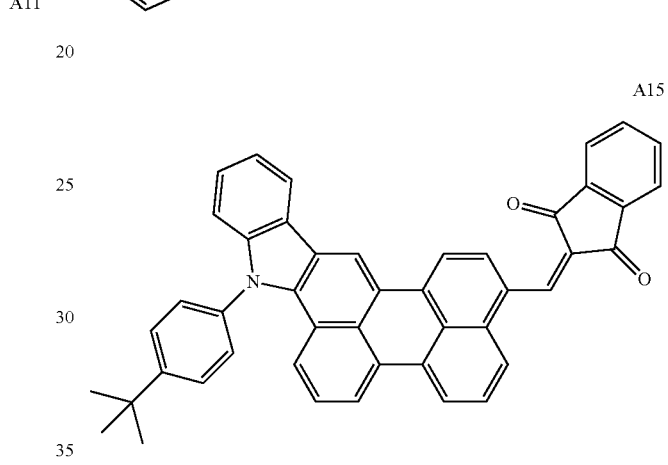
A15
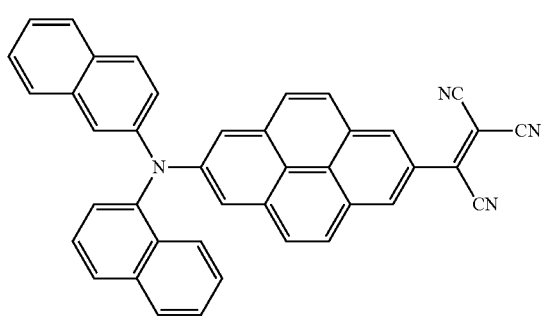
A12
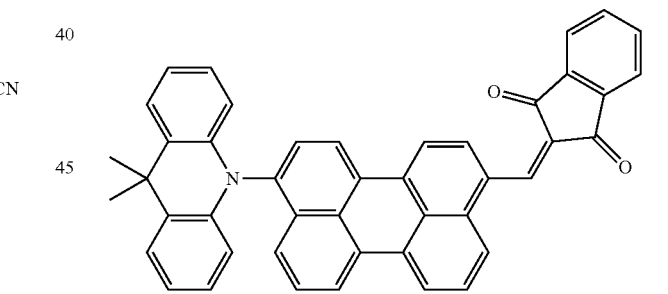
A16
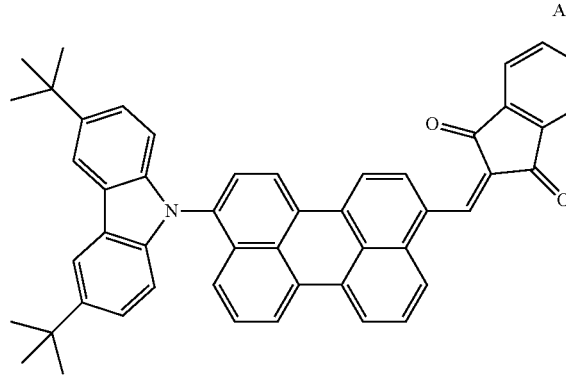
A13
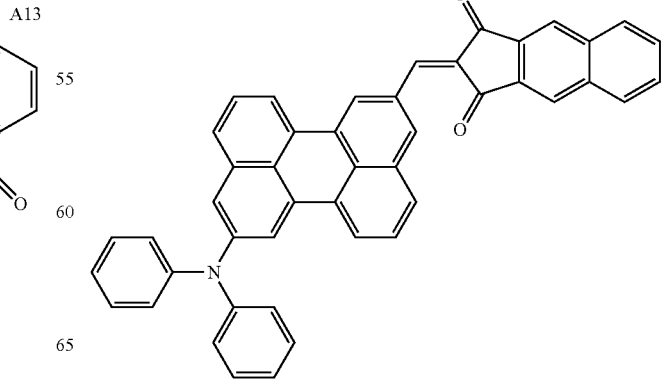
A17

-continued
A18
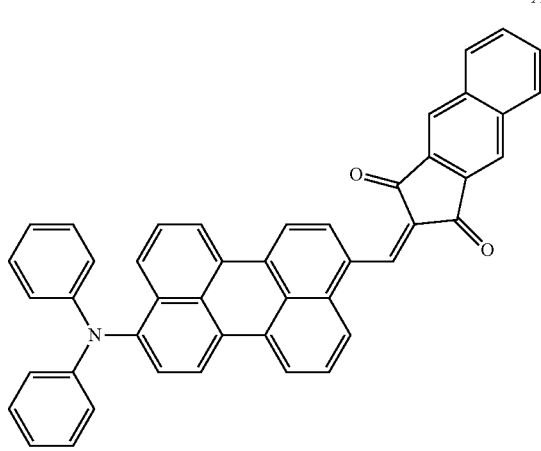
A19
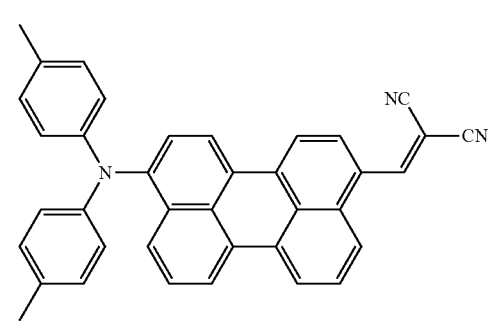
A20
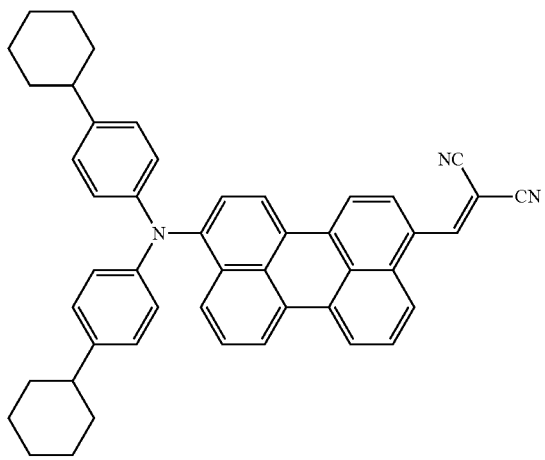
A21
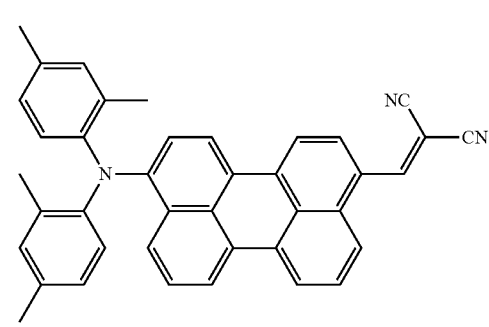
-continued
A22
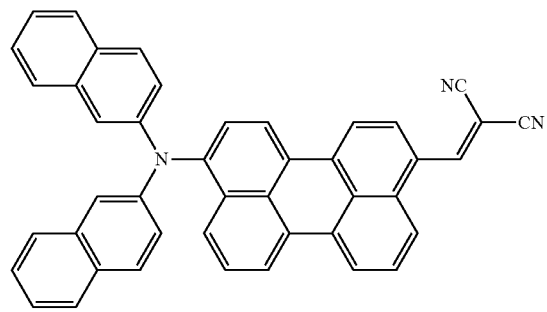
A23
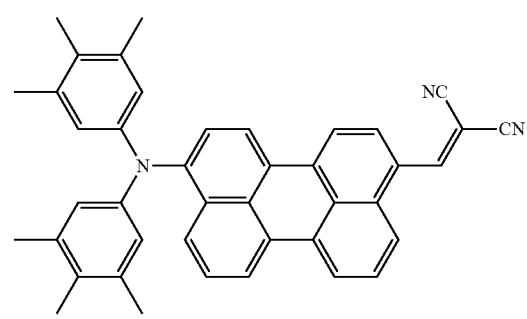
A24
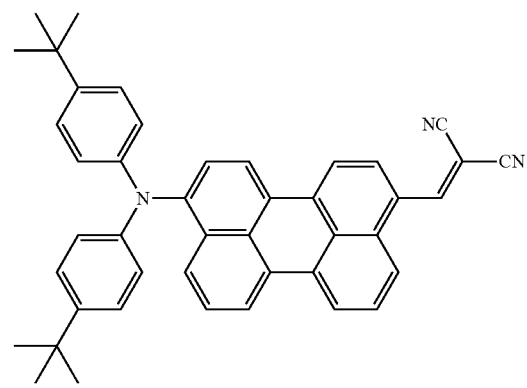
A25
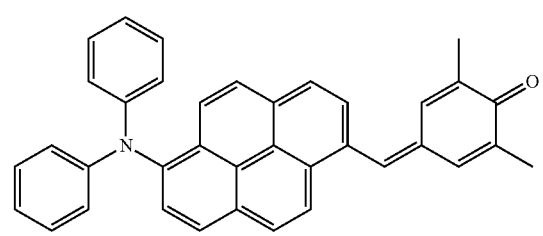

-continued
A26
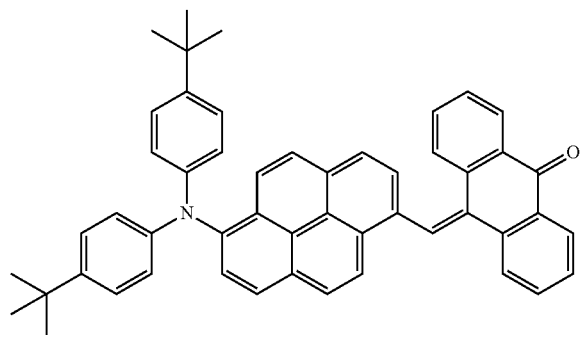
A27
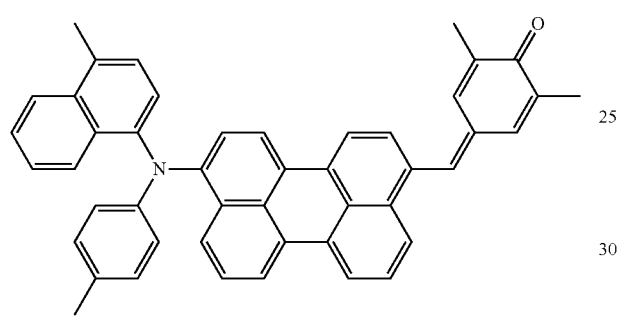
A28
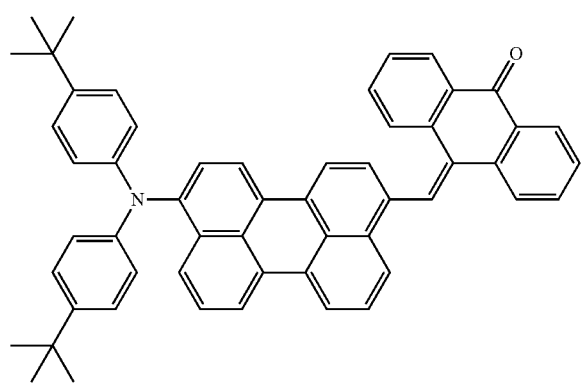
A29
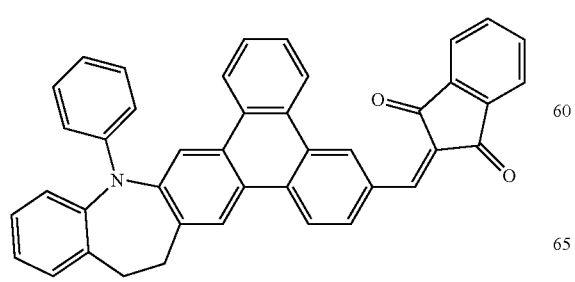
-continued
A30
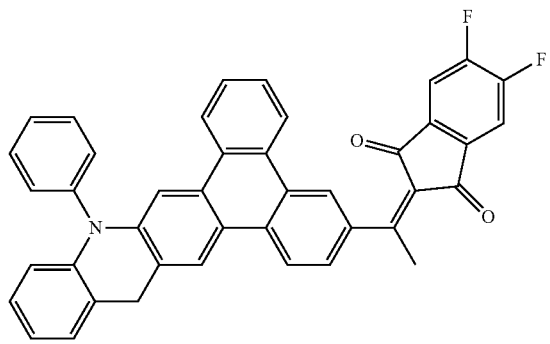
A31
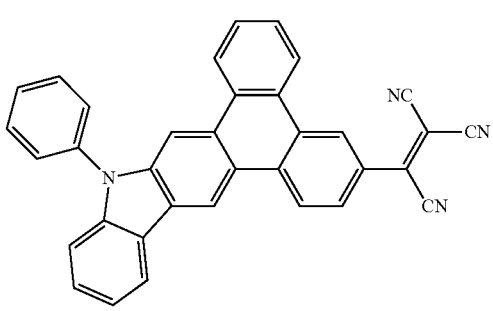
A32
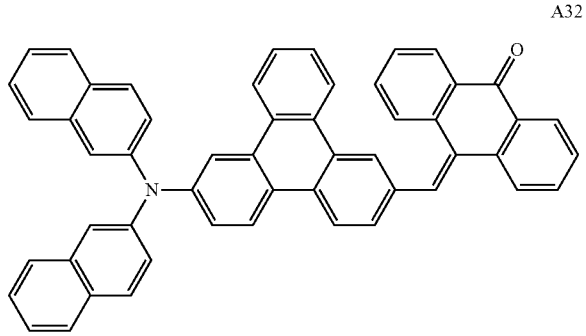
A33
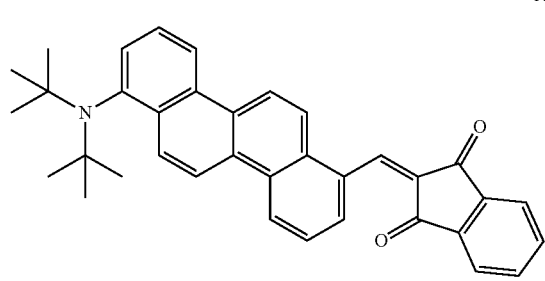

A34
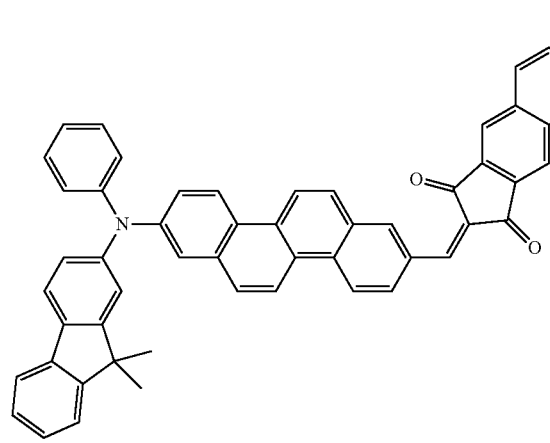
B2
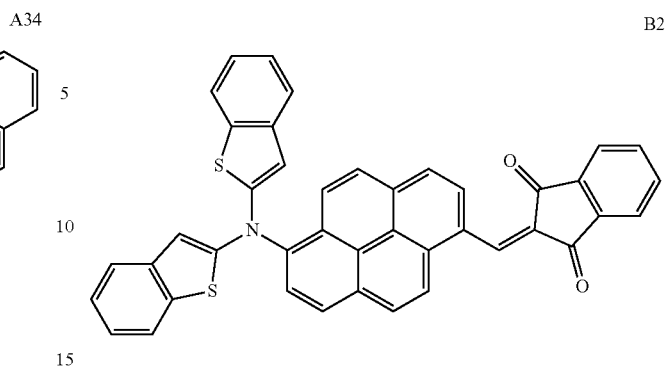
A35
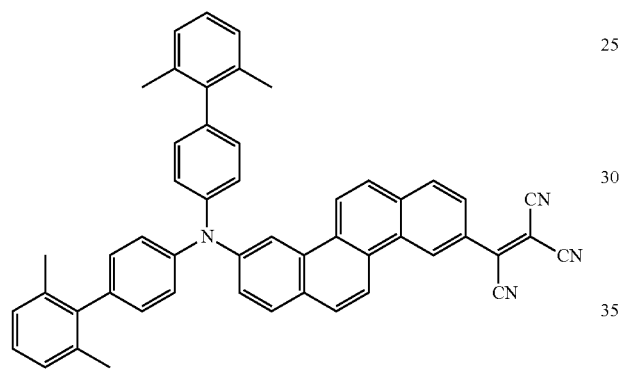
B3
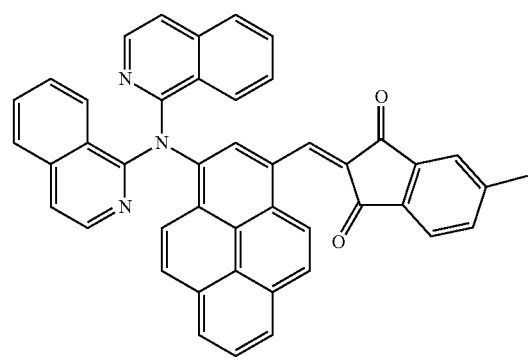
A36
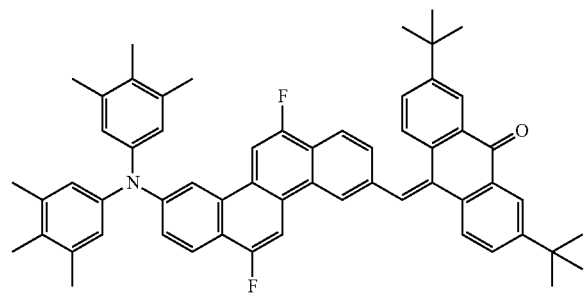
B4
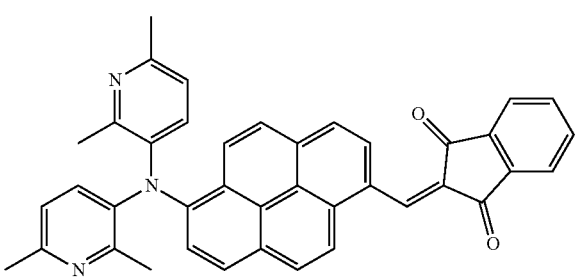
B1
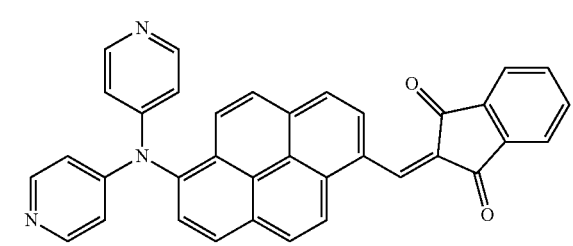
B5
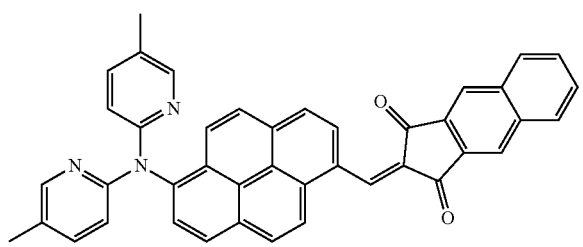

-continued
B6
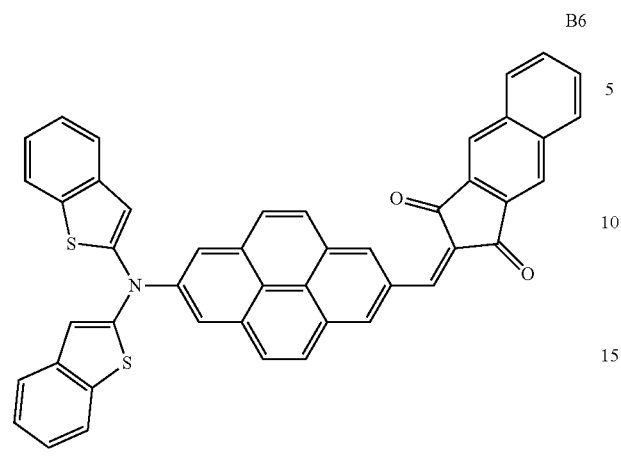
B7
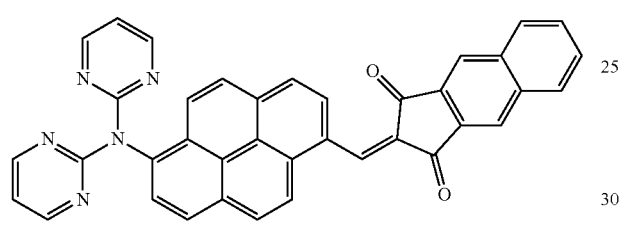
B8
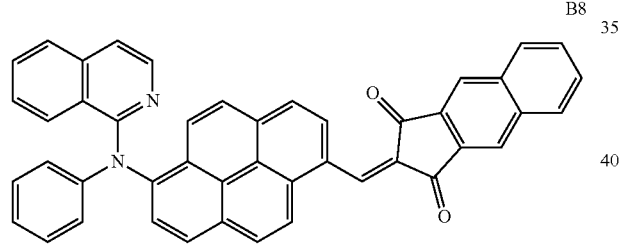
B9
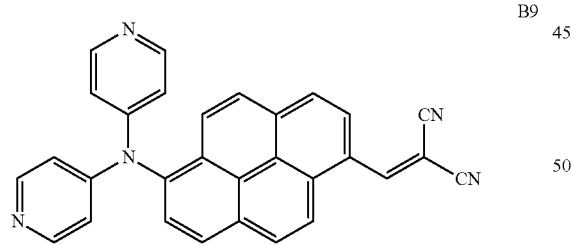
B10
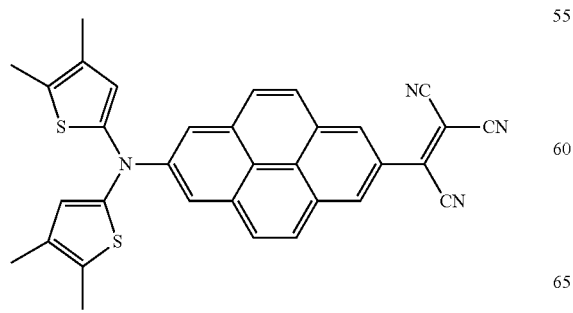
-continued
B11
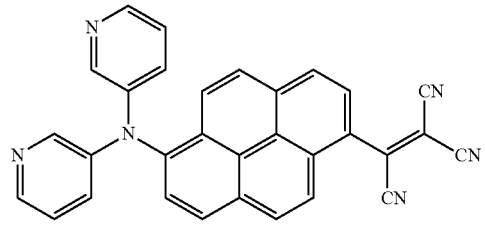
B12
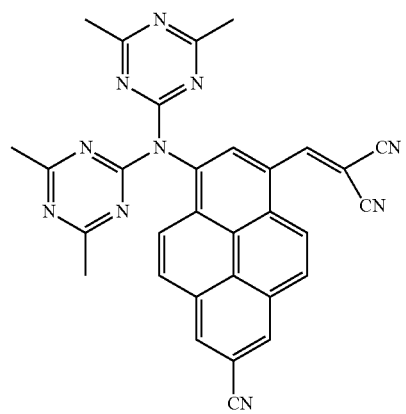
B13
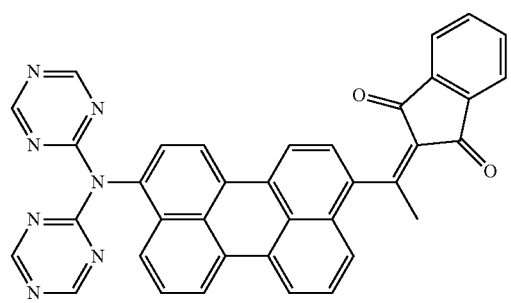
B14
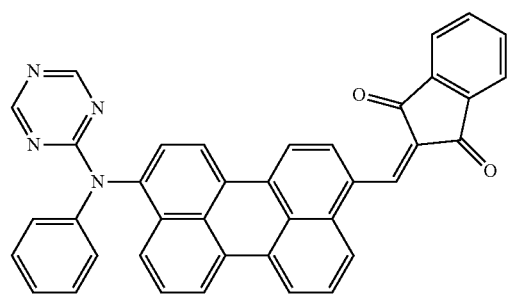

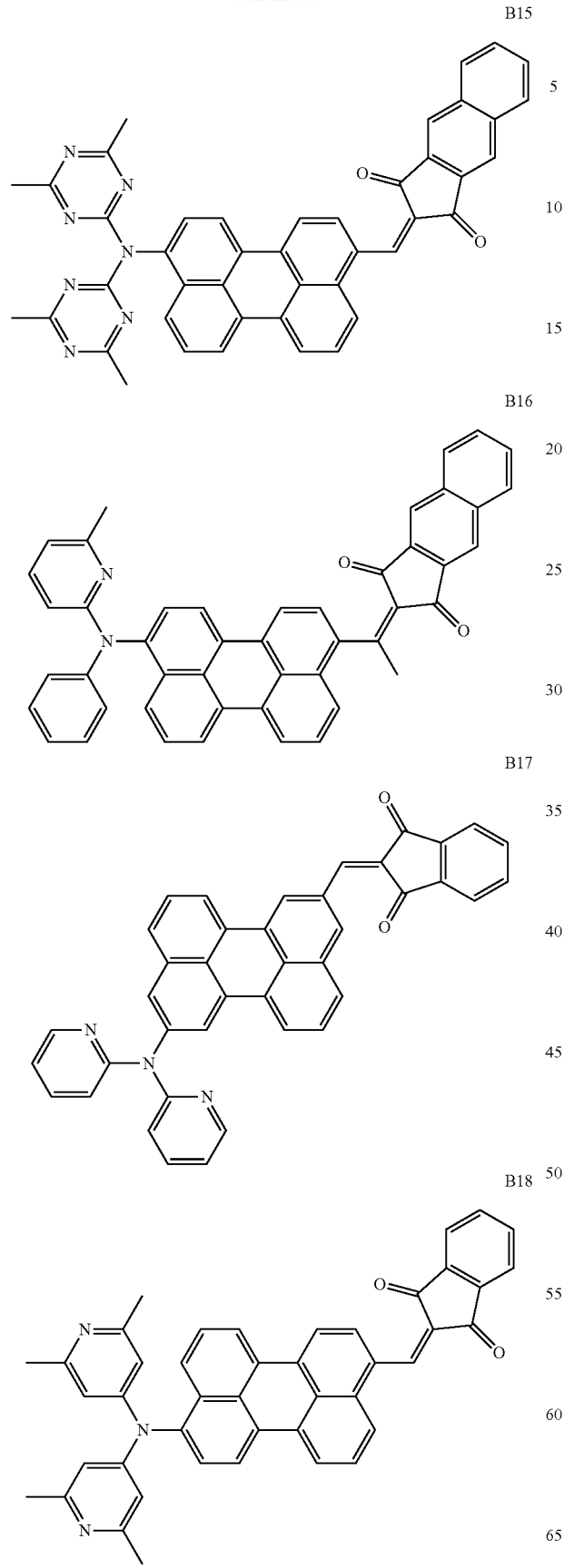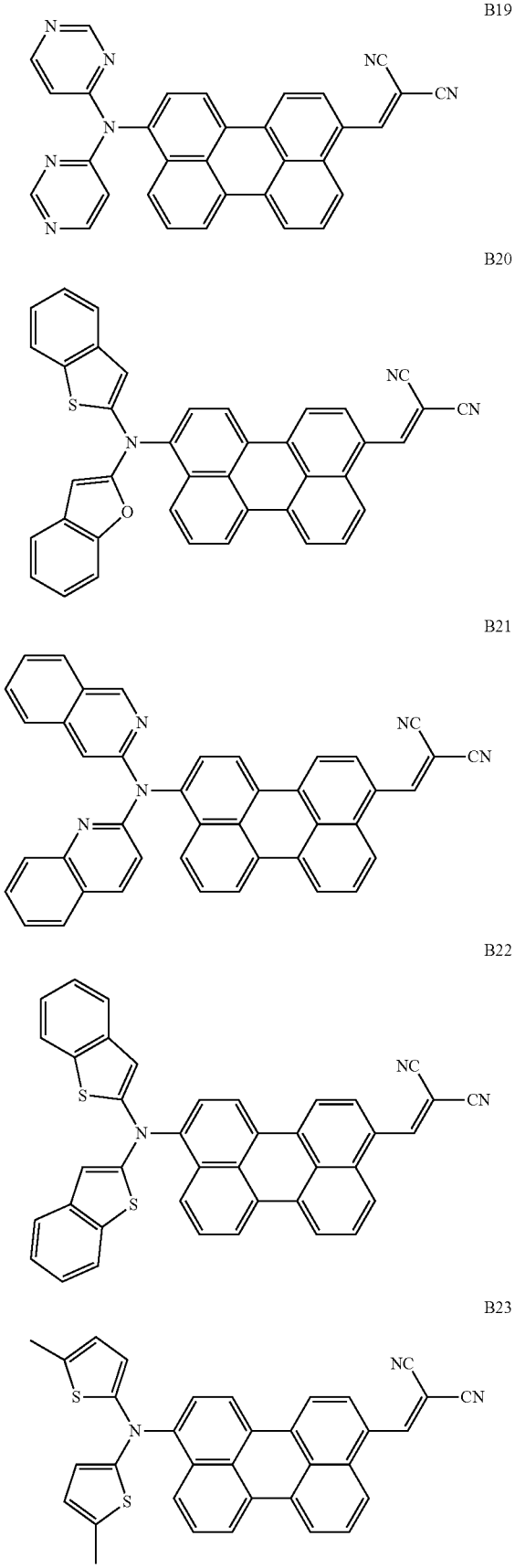

B24
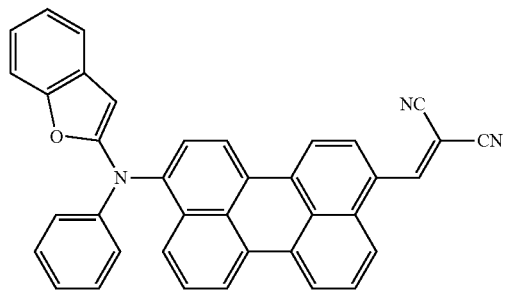
B28
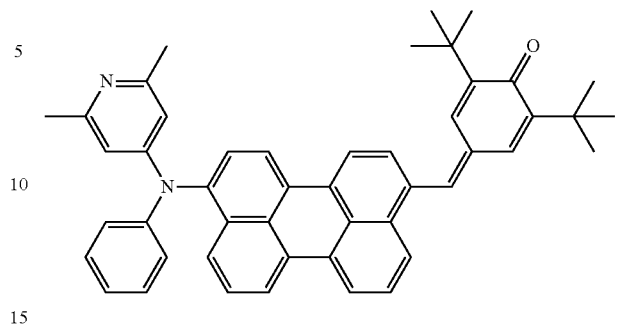
B25
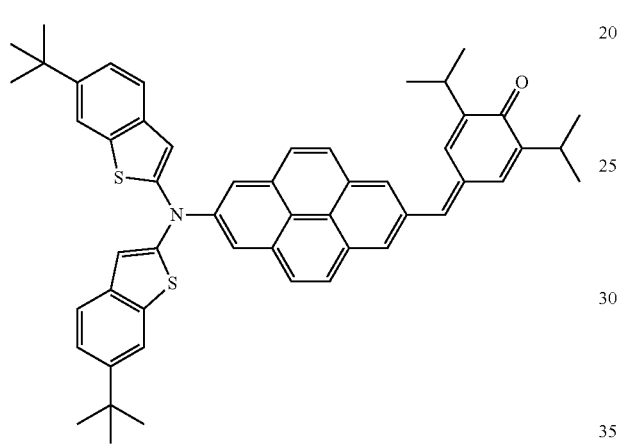
B29
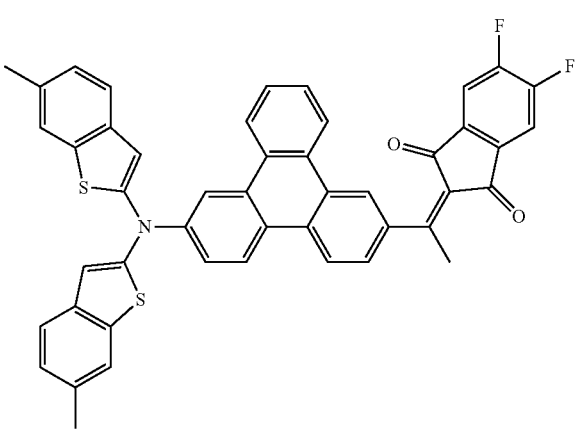
B26
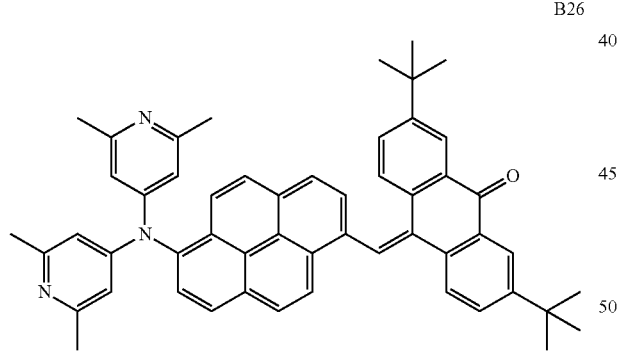
B30
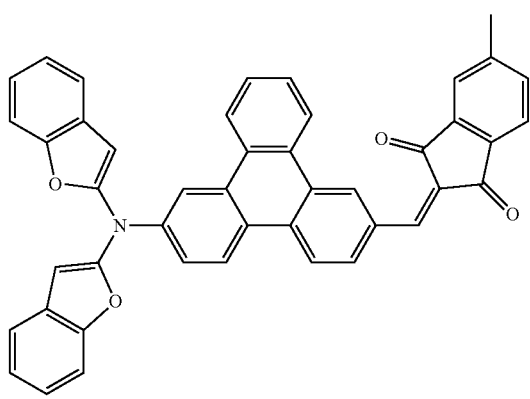
B27
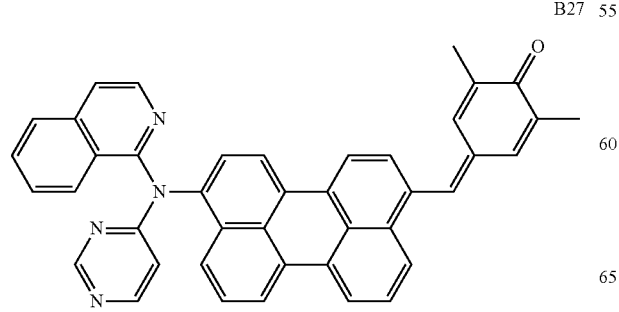
B31
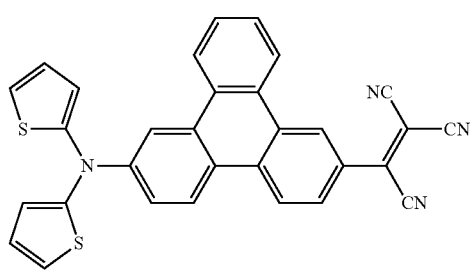

B32

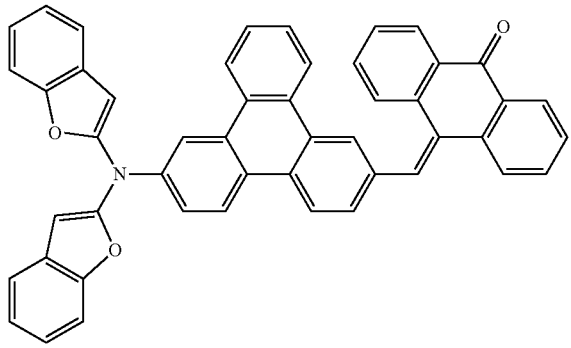

B33

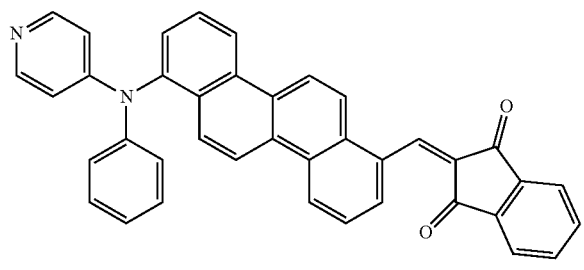

B34

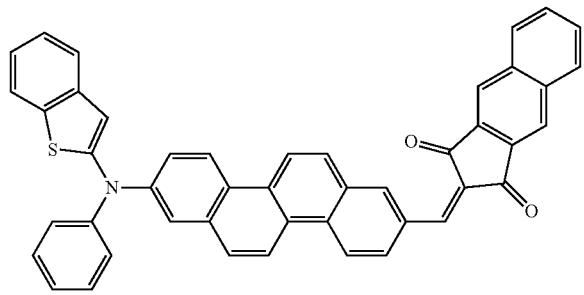

B35

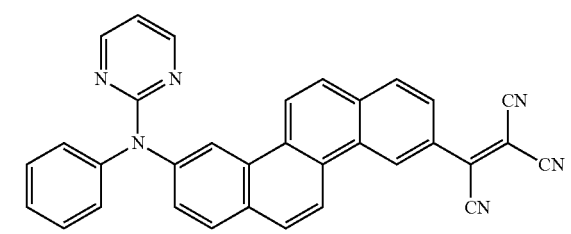

B36

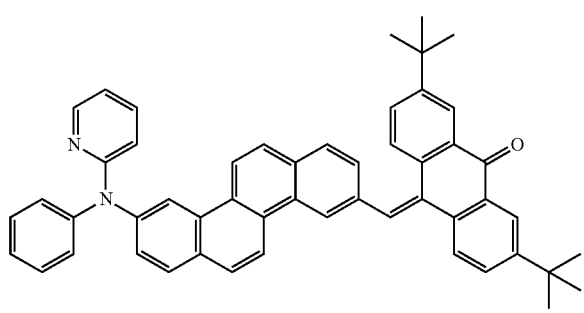

Of the compounds exemplified above, compounds each having a number preceded by A, that is, compounds belonging to Group A are each a compound in which $Ar_1$ and $Ar_2$ in the formula [1] each represent an aromatic hydrocarbon group having 6 to 18 carbon atoms that may have a substituent, or an alkyl group having 1 to 8 carbon atoms that may have a substituent. By virtue of the presence of any one of those substituents, the chemical stability of the compound itself is enhanced, and hence each of the compounds belonging to Group A is a compound excellent in thermal stability and sublimability.

Of those compounds, Exemplified Compounds A1 to A12 are each a compound in which $Ar_3$ in the formula [1] represents a pyrenediyl group and Q in the formula [1] represents any one of the general formulae [2a] to [2c], and hence are each a compound particularly excellent in thermal stability and sublimability. In addition, Exemplified Compounds A13 to A24 are each a compound in which $Ar_3$ in the formula [1] represents a perylenediyl group and the substituent Q is any one of the general formulae [2a] to [2c], and hence are each a compound particularly excellent in shifting of the maximum absorption wavelength to longer wavelengths and sublimability. Further, Exemplified Compounds A3, A4, A15, and A16 are each a compound in which $Ar_1$ and $Ar_2$, or $Ar_2$ and $Ar_3$ are bonded to each other via a single bond, or a methylene group or an ethylene group that may have an alkyl group (e.g., a methyl group), to thereby form a ring structure. The formation of the ring structure increases the melting point of the compound itself, and hence the compound is excellent in thermal stability.

Of the exemplified compounds, compounds each having a number preceded by B, that is, compounds belonging to Group B are each a compound in which any one of $Ar_1$ and $Ar_2$ in the formula [1] represents a heteroaromatic ring group having 3 to 15 carbon atoms that may have a substituent. In this case, when the heteroaromatic ring has a nitrogen atom, the electron-withdrawing property of the nitrogen atom raises the oxidation potential of the compound itself (in other words, deepens the oxidation potential), and hence the compound becomes stable against oxidation. In addition, when the heteroaromatic ring has a sulfur atom or an oxygen atom, the sulfur atom or the oxygen atom has many unshared electron pairs, and hence an intermolecular interaction is increased, resulting in a compound excellent in carrier transport ability. That is, compounds belonging to Group B are each a compound particularly excellent in terms of stability and carrier transport property based on an electronic effect.

Of those, Exemplified Compounds B1 to B12 are each a compound in which $Ar_3$ in the formula [1] represents a pyrenediyl group and Q in the formula [1] represents any one of the general formulae [2a] to [2c], and hence are each a compound particularly excellent in thermal stability and sublimability. In addition, Exemplified Compounds B13 to B24 are each a compound in which $Ar_3$ in the formula [1] represents a perylenediyl group and Q in the formula [1] represents any one of the general formulae [2a] to [2c], and hence are each a compound particularly excellent in shifting of the maximum absorption wavelength to longer wavelengths and sublimability.

(2-2) Material other than Compound of General Formula [1] contained in First Organic Compound Layer The first organic compound layer 10 may be a layer formed only of the compound of the general formula [1]. This is because the compound of the general formula [1] has a function of absorbing visible light to produce an exciton, and a function of producing/transporting charges, namely a hole and an electron from the exciton. In particular, the compound has an excellent function of absorbing visible light to produce an exciton.

However, in the present invention, the first organic compound layer 10 may contain a material other than the compound of the general formula [1]. Examples of the other material in this case include a light-absorbing material having a function of absorbing visible light to produce an exciton and a photoelectric conversion-inducing material having a function of producing/transporting charges, namely a hole and an electron from the exciton of the light-absorbing material. In this case, when the first organic compound layer 10 contains the material (the light-absorbing material or the photoelectric conversion-inducing material) other than the compound of the general formula [1], the first organic compound layer 10 may contain one kind or two or more kinds of light-absorbing materials, and may contain one kind or two or more kinds of photoelectric conversion-inducing materials. In addition, when the photoelectric converter contains the material (the light-absorbing material or the photoelectric conversion-inducing material) other than the compound of the general formula [1], the photoelectric converter may be a laminate in which the first organic compound layer 10 containing the compound of the general formula [1] and a layer containing the other material are laminated. When the photoelectric converter is constituted of a laminate in which a plurality of layers are laminated as described above, the layers constituting the laminate are preferably laminated in a direction running from the electron-collecting electrode 14 toward the hole-collecting electrode 13.

Examples of the photoelectric conversion-inducing material other than the compound of the general formula [1] include n-type organic semiconductors, specifically, a fullerene derivative, a naphthalene compound, such as NTCDI, a perylene compound, such as PTCDI, a phthalocyanine compound, such as SubPc, and a thiophene compound, such as DCV3T. Of those photoelectric conversion-inducing materials, a fullerene derivative is preferred. This is because the fullerene derivative is a material having a particularly excellent function of producing/transporting charges (hole and electron) from an exciton among the above-mentioned n-type organic semiconductors, and also having a function of absorbing visible light to produce an exciton. Those photoelectric conversion-inducing materials may be used alone or in combination thereof.

A fullerene serving as a skeleton that fullerene derivatives have in common is a collective term for hollow closed-shell clusters constituted only of many carbon atoms. In addition, specific examples of the fullerene include C60 and higher fullerenes, such as C70, C74, C76, and C78.

The fullerene derivative is a compound obtained by introducing a substituent, such as an alkyl group, an aryl group, or a heterocyclic group, into the fullerene. In the following description, the fullerene and the fullerene derivative are sometimes collectively referred to as "fullerene etc.". Those compounds may be selected and used alone or in combination thereof.

The fullerene etc. contained in the first organic compound layer 10 may be used as an n-type organic semiconductor. In addition, molecules of the fullerene etc. cause stacking between fluoranthene skeletons, and hence the molecules can be lined up (aligned) in a certain direction in the first organic compound layer 10. With this, an electron pathway is formed, and hence an electron-transporting property is improved to improve the high-speed responsiveness of the organic photoelectric conversion element. The content of the fullerene etc. in the first organic compound layer 10 is preferably 20 vol % or more and 80 vol % or less with respect to the entirety of the first organic compound layer 10.

Examples of the fullerene etc. (the fullerene or the fullerene derivative) that may be incorporated into the first organic compound layer 10 include fullerene C60, fullerene C70, fullerene C76, fullerene C78, fullerene C80, fullerene C82, fullerene C84, fullerene C90, fullerene C96, fullerene C240, fullerene 540, a mixed fullerene, a fullerene nanotube, and fullerene derivatives shown below.

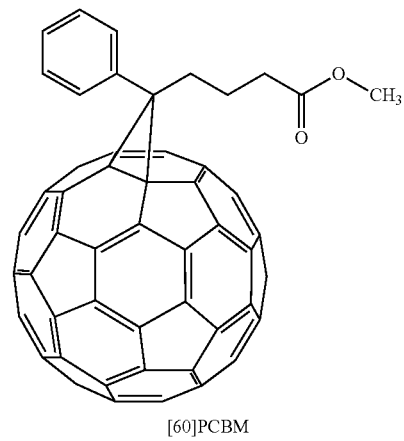

[60]PCBM

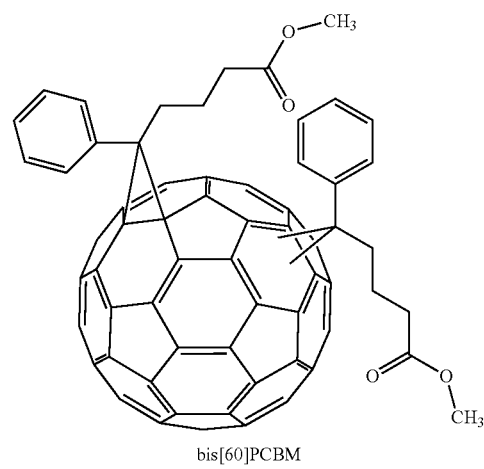

bis[60]PCBM

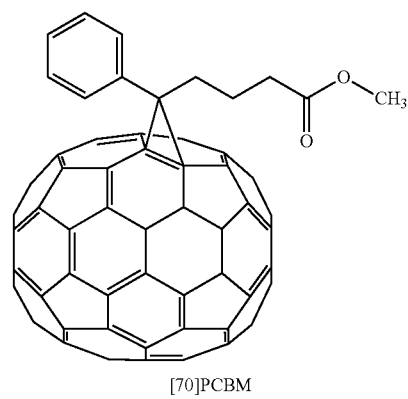

[70]PCBM

-continued

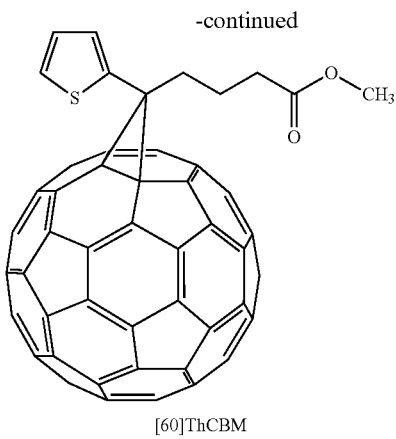

[60]ThCBM (3) Constituent Materials for Members other than First Organic Compound Layer Next, constituent materials for members, other than the first organic compound layer, constituting the organic photoelectric conversion element of the present invention are described.

(3-1) Substrate

The organic photoelectric conversion element of the present invention may include a substrate, which is not shown in FIG. 1. Examples of the substrate include a silicon substrate, a glass substrate, and a flexible substrate.

(3-2) Hole-Collecting Electrode

The constituent material for the hole-collecting electrode 13 is not particularly limited as long as the constituent material is a material having high conductivity and having transparency.

Specific examples thereof include a metal, a metal oxide, a metal nitride, a metal boride, an organic conductive compound, and a mixture obtained by combining two or more kinds thereof. More specific examples thereof include: conductive metal oxides, such as antimony-doped or fluorine-doped tin oxide (ATO or FTO), tin oxide, zinc oxide, indium oxide, indium tin oxide (ITO), and indium zinc oxide; metal materials, such as gold, silver, chromium, nickel, titanium, tungsten, and aluminum; conductive compounds, such as oxides or nitrides of these metal materials (e.g., titanium nitride (TiN)); mixtures or laminates of these metals and the conductive metal oxides; inorganic conductive substances, such as copper iodide and copper sulfide; organic conductive materials, such as polyaniline, polythiophene, and polypyrrole; and laminates of these substances or materials and ITO or titanium nitride. The constituent material for the hole-collecting electrode 13 is particularly preferably a material selected from titanium nitride, molybdenum nitride, tantalum nitride, and tungsten nitride.

(3-3) Electron-Collecting Electrode

Specific examples of the constituent material for the electron-collecting electrode 14 include ITO, zinc indium oxide, $SnO_2$, antimony-doped tin oxide (ATO), ZnO, Al-doped zinc oxide (AZO), gallium-doped zinc oxide (GZO), $TiO_2$, and fluorine-doped tin oxide (FTO).

A method of forming each of the above-mentioned two kinds of electrodes (13 and 14) may be appropriately selected in consideration of its suitability with an electrode material to be used. Specifically, the electrodes may be formed by, for example, a printing system, a wet system, such as a coating system, a physical system, such as a vacuum deposition method, a sputtering method, or an ion plating method, or a chemical system, such as CVD or a plasma CVD method.

In the case where the electrodes (13 and 14) are formed by using ITO, the electrodes may be formed by a method such as an electron beam method, the sputtering method, a resistance heating deposition method, a chemical reaction method (e.g., a sol-gel method), or the application of a dispersed product of indium tin oxide. In addition, in such case, the surfaces of the formed electrodes (ITO electrodes) may be subjected to, for example, a UV-ozone treatment or a plasma treatment. In the case where the electrodes (13 and 14) are formed by using TiN, various film-forming methods typified by a reactive sputtering method may be used. In addition, in such case, the formed electrodes (TiN electrodes) may be subjected to, for example, an annealing treatment, the UV-ozone treatment, or the plasma treatment.

(3-4) Second Organic Compound Layer

In the organic photoelectric conversion element of the present invention, an example of the constituent material for the second organic compound layer 11 is an organic compound to be used as a hole-transporting material or a hole-injecting material.

(3-5) Third Organic Compound Layer

In the organic photoelectric conversion element of the present invention, an example of the constituent material for the third organic compound layer 12 is a material having a high ionization potential, specifically an organic compound to be used as an electron-transporting material or an electron-injecting material. The fullerene etc., which is one of the constituent materials for the first organic compound layer 10, is a material excellent in electron-transporting property as described above, and hence may be used as the constituent material for the third organic compound layer 12.

2. Applications of Organic Photoelectric Conversion Element of the Present Invention The organic photoelectric conversion element of the present invention can provide organic photoelectric conversion elements corresponding to light beams having different wavelengths through appropriate setting of the constituent materials for the first organic compound layer. As used herein, the term "wavelength" refers to the wavelength of light to be received by a predetermined organic photoelectric conversion element. In the case where a plurality of kinds of organic photoelectric conversion elements corresponding to different wavelengths are provided as described above, when the plurality of kinds of organic photoelectric conversion elements are laminated in a direction running from the hole-collecting electrode toward the electron-collecting electrode, an organic photoelectric conversion apparatus that does not need the color filter illustrated in FIG. 1 is obtained. At least one kind of organic photoelectric conversion element of the plurality of kinds of organic photoelectric conversion elements included in the organic photoelectric conversion apparatus is the organic photoelectric conversion element according to the present invention.

The organic photoelectric conversion element according to the present invention may be used as a constituent member of a light area sensor by being two-dimensionally arranged in an in-plane direction. The light area sensor includes a plurality of organic photoelectric conversion elements, and the plurality of organic photoelectric conversion elements are arranged so that a plurality thereof are arranged in each of a row direction and a column direction. The organic photoelectric conversion elements to be included in the light area sensor may be replaced with the above-mentioned organic photoelectric conversion apparatus.

The organic photoelectric conversion element according to the present invention may be used as a constituent member for an imaging element. The imaging element includes a plurality of organic photoelectric conversion elements each serving as a light-receiving pixel, and a transistor connected to each of the organic photoelectric conversion elements. As used herein, the term "transistor" refers to a transistor configured to read out a charge generated from the organic photoelectric conversion element. Information based on the charge read out by the transistor is transferred to a sensor unit connected to the imaging element. Examples of the sensor unit include a CMOS sensor and a CCD sensor. Through the collection of pieces of information acquired in the respective light-receiving pixels into the sensor unit, an image can be obtained.

The imaging element may include, for example, an optical filter, such as a color filter, so as to correspond to each light-receiving pixel. When the organic photoelectric conversion element corresponds to light having a specific wavelength, the imaging element preferably includes a color filter configured to transmit light in a wavelength region to which the organic photoelectric conversion element can correspond. One color filter may be arranged for each light-receiving pixel, or one color filter may be arranged for a plurality of light-receiving pixels.

The optical filter included in the imaging element is not limited to the color filter, and other examples of the optical filter that may be used include a low-pass filter configured to transmit light having a wavelength equal to or longer than an infrared wavelength, and a UV-cut filter and a long-pass filter each configured to transmit light having a wavelength equal to or shorter than an ultraviolet wavelength.

The imaging element may include an optical member, such as a microlens, so as to, for example, correspond to each light-receiving pixel. The microlens included in the imaging element is a lens configured to concentrate external light on the photoelectric converter included in the organic photoelectric conversion element included in the imaging element. One microlens may be arranged for each light-receiving pixel, or one microlens may be arranged for a plurality of light-receiving pixels. When a plurality of light-receiving pixels are arranged, it is preferred that one microlens be arranged for a plurality (predetermined number of 2 or more) of light-receiving pixels.

The organic photoelectric conversion element according to the present invention may be used for an imaging apparatus. The imaging apparatus includes an imaging optical system including a plurality of lenses, and an imaging element configured to receive light that has passed through the imaging optical system. In addition, the imaging apparatus may be an imaging apparatus including: a joining portion capable of being joined to the imaging optical system; and an imaging element. As used herein, the term "imaging apparatus" more specifically refers to a digital camera or a digital still camera.

In addition, the imaging apparatus may further include a receiving unit configured to receive an external signal. The signal to be received by the receiving unit is a signal configured to control at least one of the imaging range of the imaging apparatus, the start of the imaging thereof, and the end of the imaging. In addition, the imaging apparatus may further include a transmitting unit configured to transmit an image acquired by imaging to the outside. When including the receiving unit and the transmitting unit as described above, the imaging apparatus can be used as a network camera.

EXAMPLES

[Synthesis Example 1] Synthesis of Exemplified Compound A2

Exemplified Compound A2 was synthesized in accordance with the following synthesis scheme.

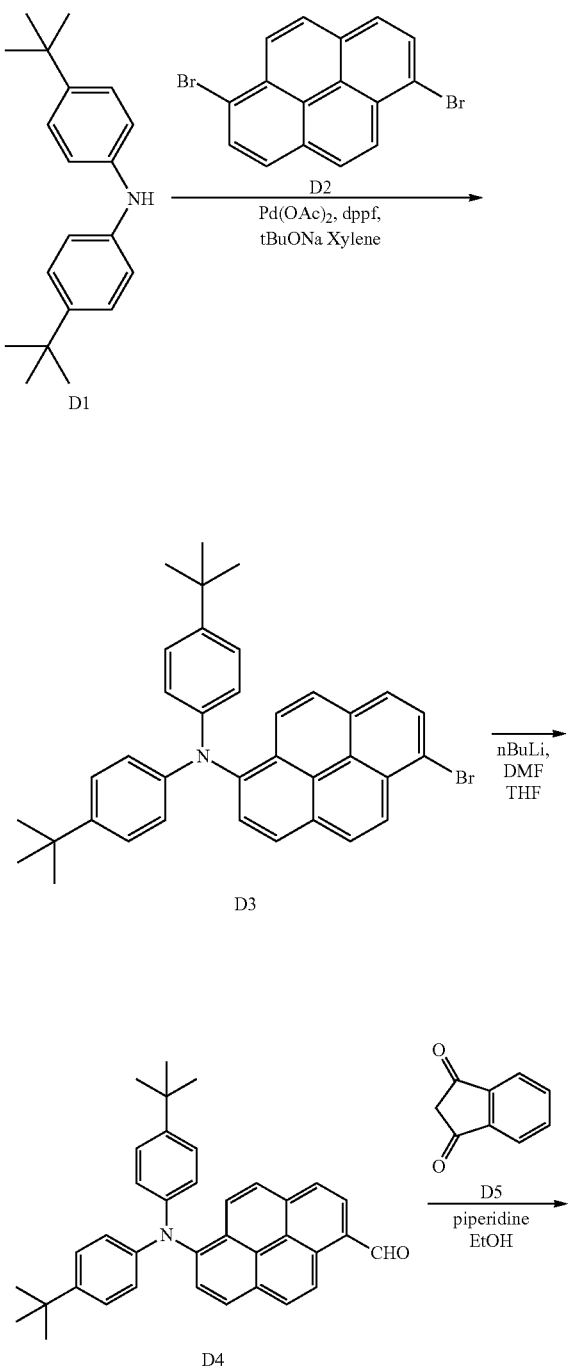

-continued

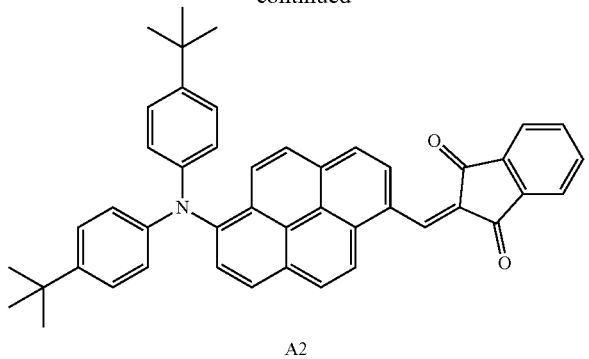

A2

(1) Synthesis of Compound D3

A 500 mL recovery flask was loaded with the following reagents and solvent.
Compound D1: 2.00 g (7.11 mmol)
Compound D2: 3.84 g (10.6 mmol)
Palladium acetate: 127 mg (0.57 mmol)
1,1-Bis(diphenylphosphino)ferrocene: 788 mg (1.42 mmol)
Sodium tert-butoxide: 1.37 g (14.2 mmol)
Anhydrous xylene: 400 ml Next, under nitrogen, the reaction solution was heated to reflux for 7 hours while being stirred. After the completion of the reaction, the solution was filtered through a membrane filter to provide a filtrate. The resultant filtrate was washed with water, and dried over sodium sulfate, and then the filtrate was concentrated under reduced pressure to provide a crude product. Next, the crude product was purified by silica gel column chromatography (developing solvent: toluene/heptane=1/1) to provide 2.55 g of Compound D3 (yield: 64%).

(2) Synthesis of Compound D4

A 200 mL three-necked flask was loaded with the following reagent and solvent.
Compound D3: 2.00 g (3.57 mmol)
Anhydrous THF: 100 ml Next, the reaction solution was stirred under a nitrogen atmosphere at −80° C. for 1 hour. Next, 3.30 ml (5.36 mmol) of n-butyllithium was slowly added dropwise, and then the reaction solution was further stirred for 1 hour. Next, to the stirred reaction solution, 0.55 ml (7.14 mmol) of anhydrous DMF was slowly added dropwise. After the completion of the dropwise addition, the temperature of the reaction solution was gradually increased to room temperature. Next, 30 ml of a 0.1 N aqueous solution of hydrochloric acid was added to the reaction solution, and then an extraction operation was performed using chloroform. The organic layer obtained by the extraction operation was dried over sodium sulfate, and then the organic layer was concentrated under reduced pressure to provide a crude product. Next, the crude product was purified by silica gel column chromatography (developing solvent: toluene/heptane=2/1) to provide 1.05 g of Compound D4 (yield: 58%).

(3) Synthesis of Exemplified Compound A2

A 200 mL recovery flask was loaded with the following reagents and solvent.
Compound D4: 500 mg (0.98 mmol)
Compound D5: 215 mg (1.47 mmol)
Piperidine: several drops
Ethanol: 50 ml Next, under a nitrogen atmosphere, the reaction solution was heated to reflux for 7 hours while being stirred. After the completion of the reaction, the solution was filtered through a membrane filter to provide a crude product. Next, the crude product was purified by silica gel column chromatography (developing solvent: toluene/heptane=2/1) to provide 262 mg of Exemplified Compound A2 (yield: 42%).

The obtained Exemplified Compound A2 was identified by the following method.

[Matrix-assisted laser desorption/ionization time-of-flight mass spectrometry (MALDI-TOF-MS) (AutoFlex LRF (product name) manufactured by Bruker)]

Found: m/z=637.51, calcd.: $C_{46}H_{39}NO_2$=637.81 [UV-visible absorption spectrum measurement].

The obtained Exemplified Compound A2 was measured for its UV-visible absorption spectrum, and as a result, was found to have a maximum absorption wavelength ($\lambda_{max}$) of 546 nm.

[Synthesis Example 2] Synthesis of Exemplified Compound A1

Exemplified Compound A1 was obtained by performing synthesis by the same method as in Synthesis Example 1 with the exception that, in Synthesis Example 1(1), the following Compound D6 was used in place of Compound D1.

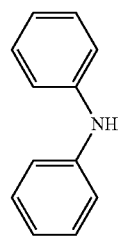

D6

The obtained compound was identified. The results are shown below.

[MALDI-TOF-MS]

Found: m/z=525.87, calcd.: $C_{38}H_{23}NO_2$=525.59 [UV-visible absorption spectrum measurement].

$\lambda_{max}$: 524 nm

[Synthesis Example 3] Synthesis of Exemplified Compound A5

Exemplified Compound A5 was obtained by performing synthesis by the same method as in Synthesis Example 1 with the exception that, in Synthesis Example 1(3), the following Compound D7 was used in place of Compound D5.

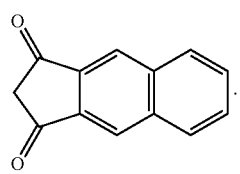

D7

The obtained compound was identified. The results are shown below.

[MALDI-TOF-MS]

Found: m/z=687.56, calcd.: $C_{50}H_{41}NO_2$=687.87 [UV-visible absorption spectrum measurement].

$\lambda_{max}$: 574 nm

[Synthesis Example 4] Synthesis of Exemplified Compound A9

A 50 ml recovery flask was loaded with the following reagents and solvent.

Compound D4: 250 mg (0.49 mmol)

Malononitrile: 48 mg (0.74 mmol)

Anhydrous dichloromethane: 10 ml

Next, several drops of triethylamine were added dropwise into the reaction solution, and then the reaction solution was stirred under room temperature for 24 hours. After the completion of the reaction, the reaction solution was washed with water, and dried over sodium sulfate, and then the solution was concentrated under reduced pressure to provide a crude product. Next, the crude product was purified by silica gel column chromatography (developing solvent: chloroform) to provide 178 mg of Exemplified Compound A9 (yield: 65%).

The obtained compound was identified. The results are shown below.

[MALDI-TOF-MS]

Found: m/z=557.86, calcd.: $C_{40}H_{35}N_3$=557.73 [UV-visible absorption spectrum measurement].

$\lambda_{max}$: 504 nm

[Synthesis Example 5] Synthesis of Exemplified Compound A19

Exemplified Compound A19 was obtained by performing synthesis by the same method as in Synthesis Example 4 with the exception that, in Synthesis Example 4, the following Compound D8 was used in place of Compound D4.

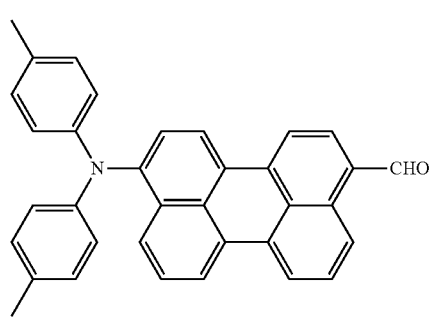

D8

The obtained compound was identified. The results are shown below.

[MALDI-TOF-MS]

Found: m/z=523.22, calcd.: $C_{38}H_{25}N_3$=523.63 [UV-visible absorption spectrum measurement].

$\lambda_{max}$: 582 nm

[Synthesis Example 6] Synthesis of Exemplified Compound A28

Exemplified Compound A28 was obtained by performing synthesis by the same method as in Synthesis Example 1 with the exception that, in Synthesis Example 1(1), the following Compound D9 was used in place of Compound D2, and in Synthesis Example 1(3), the following Compound D10 was used in place of Compound D5.

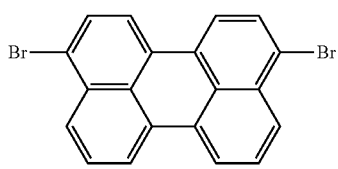

D9

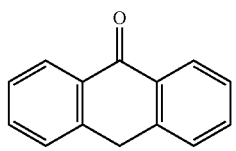

D10

The obtained compound was identified. The results are shown below.

[MALDI-TOF-MS]

Found: m/z=735.72, calcd.: $C_{55}H_{45}NO$=735.95 [UV-visible absorption spectrum measurement].

$\lambda_{max}$: 569 nm

[Synthesis Example 7] Synthesis of Exemplified Compound A7

(1) Synthesis of Compound D11

A 200 mL three-necked flask was loaded with the following reagent and solvent.

Compound D3: 1.00 g (1.78 mmol)

Anhydrous THF: 50 ml

Next, the reaction solution was stirred under a nitrogen atmosphere at −80° C. for 1 hour. After that, 1.15 ml (2.68 mmol) of n-butyllithium was slowly added dropwise, and then the reaction solution was further stirred for 1 hour. After that, 0.33 ml (3.57 mmol) of anhydrous N,N-dimethylacetamide was slowly added dropwise. After the completion of the dropwise addition, the temperature of the reaction solution was gradually increased to room temperature. Next, 30 ml of a 0.1 N aqueous solution of hydrochloric acid was added to the reaction solution, and then an extraction operation was performed using chloroform. The organic layer obtained by the extraction operation was dried over sodium sulfate, and then the organic layer was concentrated under reduced pressure to provide a crude product. Next, the crude product was purified by silica gel column chromatography (developing solvent: toluene/heptane=1/2) to provide 354 mg of the following Compound D11 (yield: 38%).

D11

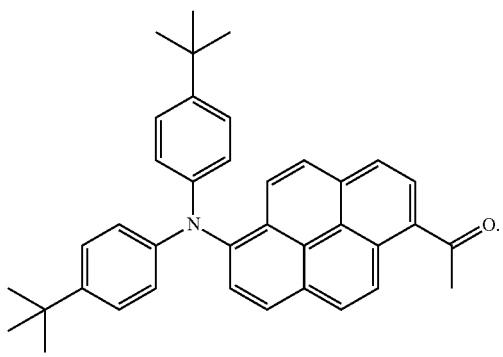

(2) Synthesis of Exemplified Compound A7

A 200 mL recovery flask was loaded with the following reagents and solvent.
Compound D11: 354 mg (0.68 mmol)
Compound D7: 198 mg (1.01 mmol)
Piperidine: several drops
Ethanol: 30 ml Next, under a nitrogen atmosphere, the reaction solution was heated to reflux for 24 hours while being stirred. After the completion of the reaction, the solution was filtered through a membrane filter to provide a crude product. Next, the crude product was purified by silica gel column chromatography (developing solvent: toluene/heptane=2/1) to provide 191 mg of Exemplified Compound A7 (yield: 40%).

The obtained compound was identified. The results are shown below.

[MALDI-TOF-MS]

Found: m/z=701.51, calcd.: $C_{51}H_{43}NO$=701.89 [UV-visible absorption spectrum measurement].

$\lambda_{max}$: 558 nm

[Synthesis Example 8] Synthesis of Exemplified Compound B4

Exemplified Compound B4 was obtained by performing synthesis by the same method as in Synthesis Example 1 with the exception that, in Synthesis Example 1(1), the following Compound D12 was used in place of Compound D1.

D12

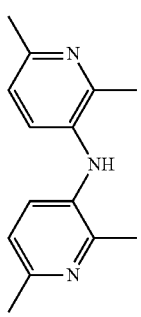

The obtained compound was identified. The results are shown below.

[MALDI-TOF-MS]

Found: m/z=583.21, calcd.: $C_{40}H_{29}N_3O_2$=583.68 [UV-visible absorption spectrum measurement].

$\lambda_{max}$: 523 nm

[Synthesis Example 9] Synthesis of Comparative Compound 1

Comparative Compound 1 was obtained by performing synthesis by the same method as in Synthesis Example 1 with the exception that, in Synthesis Example 1(1), the following Compound D13 was used in place of Compound D2. Comparative Compound 1 corresponds to Compound 1-A described in Japanese Patent Application Laid-Open No. 2010-103457.

D13

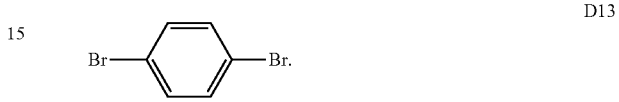

The obtained compound was identified. The results are shown below.

[MALDI-TOF-MS]

Found: m/z=401.51, calcd.: $C_{28}H_{19}NO_2$=401.46 [UV-visible absorption spectrum measurement].

$\lambda_{max}$: 484 nm

[Synthesis Example 10] Synthesis of Comparative Compound 2

Comparative Compound 2 was obtained by performing synthesis by the same method as in Synthesis Example 1 with the exception that, in Synthesis Example 1(1), the following Compound D14 was used in place of Compound D2. Comparative Compound 2 corresponds to Compound 1-B described in Japanese Patent Application Laid-Open No. 2010-103457.

D14

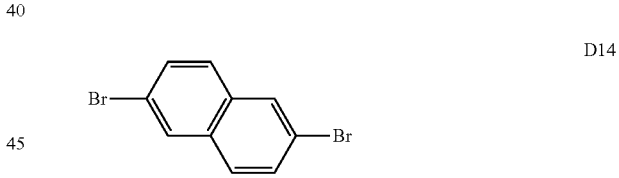

The obtained compound was identified. The results are shown below.

[MALDI-TOF-MS]

Found: m/z=451.31, calcd.: $C_{32}H_{21}NO_2$=451.51 [UV-visible absorption spectrum measurement].

$\lambda_{max}$: 498 nm

[Synthesis Example 11] Synthesis of Comparative Compound 3

An attempt was made to synthesize Comparative Compound 3 by the same method as in Synthesis Example 1 with the exception that, in Synthesis Example 1(1), the following Compound D15 was used in place of Compound D2. Comparative Compound 3 corresponds to Compound 1-C described in Japanese Patent Application Laid-Open No. 2010-103457.

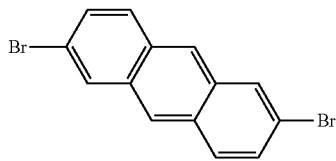

D15

After the operation of Synthesis Example 1(1) (cross-coupling reaction with the arylamine), the stability of the compound was reduced, and a reduction in purity was observed during column purification. In addition, also in the operation of Synthesis Example 1(2) (formylation reaction using n-butyllithium), the yield of the target product was remarkably reduced, and thus it was confirmed that the product itself was not stable. As a result, Comparative Compound 3 was not able to be obtained, and the production of an element containing Comparative Compound 3 was not achieved.

[Example 1] Production of Photoelectric Conversion Element

A photoelectric conversion element, in which a hole-collecting electrode, an electron-blocking layer (second organic compound layer), a photoelectric converter (first organic compound layer), a hole-blocking layer (third organic compound layer), and an electron-collecting electrode were sequentially formed on a substrate, was produced by a method described below.

First, a film of indium zinc oxide was formed on a Si substrate, and then patterned into a desired shape, to thereby form a hole-collecting electrode. In this case, the film thickness of the hole-collecting electrode was set to 100 nm. The substrate on which the hole-collecting electrode had been thus formed was used as a substrate with an electrode in the next step.

Next, organic compound layers and an electrode layer shown in Table 2 below were successively formed on the substrate with an electrode. In this case, the electrode area of the opposing electrode (electron-collecting electrode) was set to 3 mm². In addition, the following Compound Y2 was used as a constituent material Z1 for the electron-blocking layer.

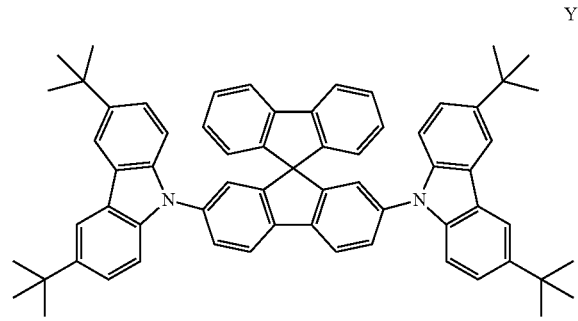

Y2

TABLE 2

| | Constituent material | Thickness [nm] |
|---|---|---|
| Second organic compound layer | Z1: Compound Y2 | 50 |
| First organic compound layer | Z2: Exemplified Compound A2 (light-absorbing material) Z3: Fullerene C60 (photoelectric conversion-inducing material) (Z2:Z3=30:70 (weight ratio)) | 200 |
| Third organic compound layer | Fullerene C60 | 10 |
| Electron-collecting electrode | Indium zinc oxide | 30 |

Thus, an organic photoelectric conversion element was obtained.

[Examples 2 to 13, and Comparative Examples 1 and 2] Production of Photoelectric Conversion Elements Organic photoelectric conversion elements were produced by the same method as in Example 1 with the exception that, in Example 1, the constituent material Z1 for the second organic compound layer, and the constituent materials Z2 and Z3 for the first organic compound layer were appropriately changed as shown in Table 2 below. The structures of Compound Y1 used in Examples 5, 10, and 12, and Compound Y3 used in Examples 3, 4, and 9 are shown below.

TABLE 3

| | Z1 | Z2 | Z3 |
|---|---|---|---|
| Example 2 | Compound Y2 | Exemplified Compound A9 | Fullerene C60 |
| Example 3 | Compound Y3 | Exemplified Compound A31 | Fullerene C60 |
| Example 4 | Compound Y3 | Exemplified Compound A1 | Fullerene C60 |
| Example 5 | Compound Y1 | Exemplified Compound A13 | Fullerene C60 |
| Example 6 | Compound Y2 | Exemplified Compound B4 | Fullerene C60 |
| Example 7 | Compound Y2 | Exemplified Compound A28 | Fullerene C60 |
| Example 8 | Compound Y2 | Exemplified Compound A7 | Fullerene C60 |
| Example 9 | Compound Y3 | Exemplified Compound A3 | Fullerene C60 |
| Example 10 | Compound Y1 | Exemplified Compound B2 | Fullerene C60 |
| Example 11 | Compound Y2 | Exemplified Compound A19 | Fullerene C70 |
| Example 12 | Compound Y1 | Exemplified Compound B5 | Fullerene C70 |
| Example 13 | Compound Y2 | Exemplified Compound A35 | Fullerene C70 |
| Comparative Example 1 | Compound Y2 | Comparative Compound 1 | Fullerene C60 |
| Comparative Example 2 | Compound Y2 | Comparative Compound 2 | Fullerene C60 |

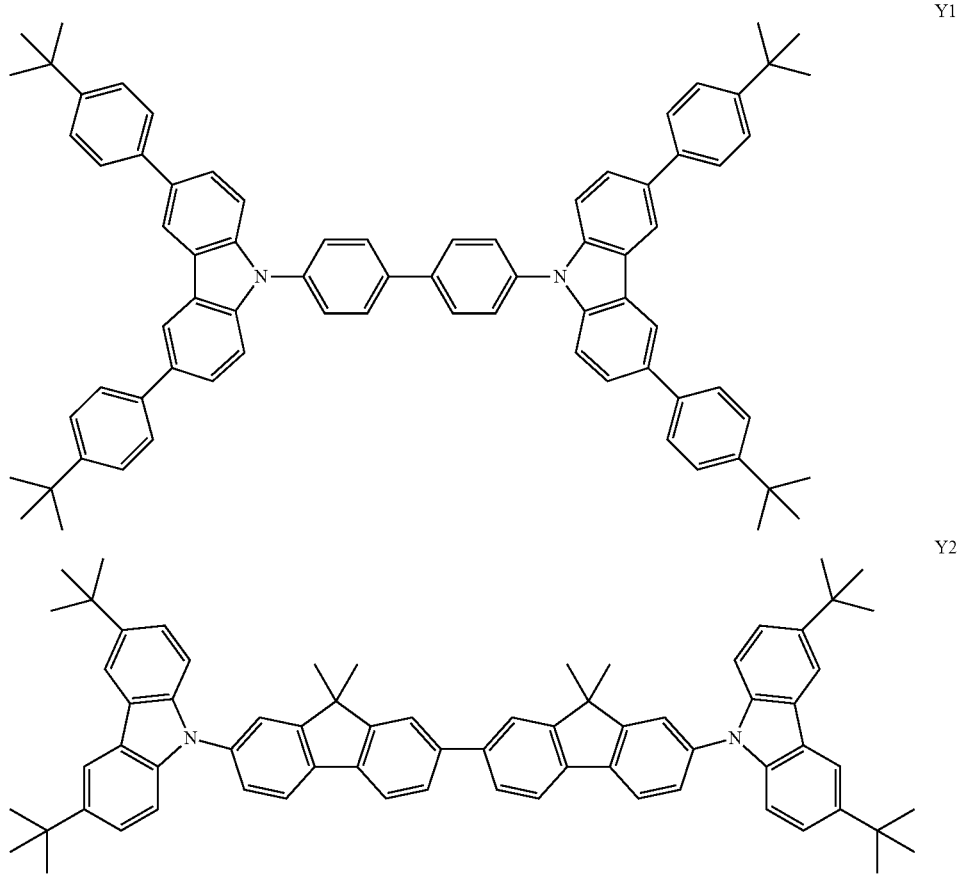

[Evaluation of Characteristics of Photoelectric Conversion Element]

For the elements obtained in Examples and Comparative Examples, characteristics of the photoelectric conversion elements were measured and evaluated.

(1) Current Characteristic

Specifically, a current flowing to an element upon application of a voltage of 5 V to the element was determined. As a result, in each of the organic photoelectric conversion elements produced in Examples, the ratio of a current in a bright place to a current in a dark place ((current in bright place)/(current in dark place)) was 100 or more. Thus, it was confirmed that each of the organic photoelectric conversion elements produced in Examples functioned satisfactorily.

(2) Quantum Yield (External Quantum Yield)

The obtained organic photoelectric conversion elements were each measured for its external quantum efficiency. The external quantum efficiency was calculated by measuring the density of a photocurrent flowing at the time of irradiation of the element with monochromatic light having an intensity of 50 μW/cm² at each of wavelengths of 450 nm, 500 nm, and 600 nm under a state in which a voltage of 5 V was applied to the element between its hole-collecting electrode and electron-collecting electrode. The photocurrent density was determined by subtracting a dark current density under a light-shielding condition from a current density under the light irradiation. The monochromatic light used for the measurement was obtained by monochromatizing white light, which had been output from a xenon lamp (product name: XB-50101AA-A, manufactured by Ushio Inc.), with a monochromator (product name: MC-10N, manufactured by Ritu Oyo Kougaku Co., Ltd.). The application of the voltage to the element and the current measurement were performed using a source meter (product name: R6243, manufactured by Advantest Corporation). In addition, in the measurement of external quantum efficiency, light was allowed to enter the element perpendicularly, and the measurement was performed from an upper electrode side. The results are shown in Table 4 below.

TABLE 4

| | External quantum yield (%) | | |
|---|---|---|---|
| | @450 nm | @500 nm | @600 nm |
| Example 1 | □ | □ | □ |
| Example 2 | □ | □ | ○ |
| Example 3 | □ | □ | ○ |
| Example 4 | □ | □ | ○ |
| Example 5 | □ | □ | ○ |
| Example 6 | □ | □ | ○ |
| Example 7 | □ | □ | ○ |
| Example 8 | □ | □ | □ |
| Example 9 | □ | □ | ○ |
| Example 10 | □ | □ | □ |
| Example 11 | □ | □ | □ |
| Example 12 | □ | □ | ○ |
| Example 13 | □ | □ | ○ |

TABLE 4-continued

| | External quantum yield (%) | | |
|---|---|---|---|
| | @450 nm | @500 nm | @600 nm |
| Comparative Example 1 | ☐ | ☐ | x |
| Comparative Example 2 | ☐ | ☐ | x |

☐: The external quantum yield is 60% or more.
o: The external quantum yield is 30% or more and less than 60%.
x: The external quantum yield is less than 30%.

It was found from Table 4 that the organic photoelectric conversion element according to the present invention had high external quantum efficiency in each of a blue region (wavelength: around 450 nm), a green region (wavelength: around 500 nm), and a red region (wavelength: around 600 nm), and hence was capable of efficiently performing photoelectric conversion throughout the entire visible light region. Meanwhile, it was found that the organic photoelectric conversion elements of Comparative Examples each had low photoelectric conversion efficiency at a wavelength of 600 nm. This results from the fact that the half width of the absorption spectrum of the light-absorbing material contained in the organic photoelectric conversion element according to the present invention is wide, and hence the material has large absorption even at a wavelength around 600 nm.

As described above in Examples, it has been found that, when the organic compound represented by the general formula [1] is contained in the photoelectric conversion layer, photoelectric conversion can be efficiently performed throughout the entire visible light region, and besides, the organic photoelectric conversion element itself is stabilized.

In the organic photoelectric conversion element according to the present invention, the photoelectric converter contains the organic compound having a wide half width of its absorption spectrum and having high stability of its structure itself. Thus, according to the present invention, the organic photoelectric conversion element having satisfactory photoelectric conversion efficiency throughout the entire visible light region, and having high stability of the element itself can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:
1. An organic photoelectric conversion element comprising:
an anode;
a cathode; and
a photoelectric converter, which is arranged between the anode and the cathode,
wherein the photoelectric converter includes at least a first organic compound layer, and
wherein the first organic compound layer contains a compound represented by general formula [1]:

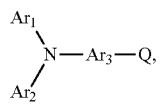

[1]

wherein, in the formula [1]:

$Ar_1$ and $Ar_2$ each represent an alkyl group having 1 to 8 carbon atoms, an aromatic hydrocarbon group having 6 to 18 carbon atoms, or a heteroaromatic ring group having 3 to 15 carbon atoms, $Ar_1$ and $Ar_2$ may each further have a substituent selected from a halogen atom, a cyano group, an alkyl group having 1 to 6 carbon atoms, a phenyl group, a tolyl group, a xylyl group, a mesityl group, and a cumenyl group, and when $Ar_1$ and $Ar_2$ each represent an aromatic hydrocarbon group having 6 to 18 carbon atoms or a heteroaromatic ring group having 3 to 15 carbon atoms, $Ar_1$ and $Ar_2$ may be bonded to each other via any one of a single bond, and a methylene group and an ethylene group each of which may have an alkyl group to form a ring structure;

$Ar_3$ represents a fused polycyclic aromatic hydrocarbon group formed by fusion of 4 or 5 six-membered rings, excluding an acene group and a 2,7-pyrene group, $Ar_3$ may further have a fluorine atom, a cyano group, a methyl group, or a tert-butyl group, and when $Ar_2$ represents an aromatic hydrocarbon group having 6 to 18 carbon atoms or a heteroaromatic ring group having 3 to 15 carbon atoms, $Ar_2$ and $Ar_3$ may be bonded to each other via any one of a single bond, and a methylene group and an ethylene group each of which may have an alkyl group to form a ring structure; and Q represents a substituent selected from a group of substituents represented by general formulae [2a] to [2e]:

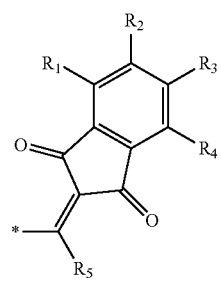

[2a]

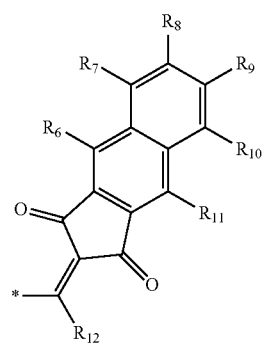

[2b]

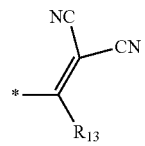

[2c]

-continued

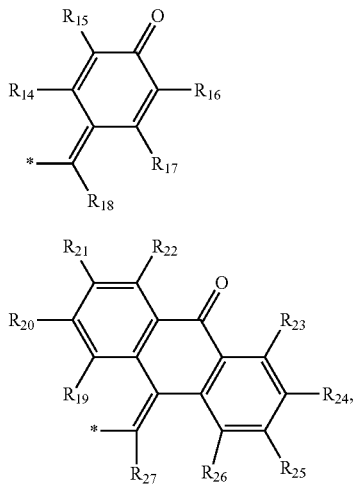

wherein, in the formulae [2a] to [2e], $R_1$ to $R_{27}$ each represents a substituent selected from a hydrogen atom, a fluorine atom, an alkyl group having 1 to 4 carbon atoms, or a cyano group, and * represents a bonding site with $Ar_3$.

2. The organic photoelectric conversion element according to claim 1, wherein the $Ar_3$ represents a pyrenediyl group, a benzopyrenediyl group, a triphenylenediyl group, a perylenediyl group, or a chrysenediyl group.

3. The organic photoelectric conversion element according to claim 1, wherein, in at least one of the $Ar_1$ and the $Ar_2$, the aromatic hydrocarbon group comprises a phenyl group or a naphthyl group, and the heteroaromatic ring group comprises a pyridyl group, a benzothienyl group, or a benzofuranyl group.

4. The organic photoelectric conversion element according to claim 1, wherein the Q represents a substituent selected from the formulae [2a] to [2c].

5. The organic photoelectric conversion element according to claim 1, wherein the first organic compound layer further contains a fullerene derivative.

6. The organic photoelectric conversion element according to claim 1, further comprising a second organic compound layer, which is arranged between the cathode and the photoelectric converter.

7. The organic photoelectric conversion element according to claim 1, further comprising a third organic compound layer, which is arranged between the anode and the photoelectric converter.

8. A light area sensor comprising a plurality of the organic photoelectric conversion elements of claim 1, wherein the plurality of the organic photoelectric conversion elements are two-dimensionally arranged in an in-plane direction.

9. An organic photoelectric conversion apparatus comprising a plurality of organic photoelectric conversion elements configured to receive light beams having different wavelengths,
wherein at least one organic photoelectric conversion element of the plurality of organic photoelectric conversion elements comprises the organic photoelectric conversion element of claim 1, and
wherein the plurality organic photoelectric conversion elements are laminated.

10. A light area sensor comprising a plurality of the organic photoelectric conversion apparatus of claim 9,
wherein the plurality of the photoelectric conversion apparatus are two-dimensionally arranged in an in-plane direction.

11. An imaging element, which is the light area sensor of claim 10, comprising:
a plurality of organic photoelectric conversion elements; and
a transistor connected to each of the plurality of organic photoelectric conversion elements,
wherein the plurality of organic photoelectric conversion elements each serve as a light-receiving pixel, and
wherein at least one of the plurality of organic photoelectric conversion elements comprises:
an anode;
a cathode; and
a photoelectric converter, which is arranged between the anode and the cathode,
wherein the photoelectric converter includes at least a first organic compound layer, and
wherein the first organic compound layer contains a compound represented by general formula [1]:

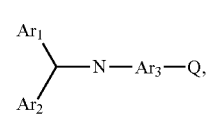

wherein, in the formula [1]:
$Ar_1$ and $Ar_2$ each represent an alkyl group having 1 to 8 carbon atoms, an aromatic hydrocarbon group having 6 to 18 carbon atoms, or a heteroaromatic ring group having 3 to 15 carbon atoms, $Ar_1$ and $Ar_2$ may each further have a substituent selected from a halogen atom, a cyano group, an alkyl group having 1 to 6 carbon atoms, a phenyl group, a tolyl group, a xylyl group, a mesityl group, and a cumenyl group, and when $Ar_1$ and $Ar_2$ each represent an aromatic hydrocarbon group having 6 to 18 carbon atoms or a heteroaromatic ring group having 3 to 15 carbon atoms, $Ar_1$ and $Ar_2$ may be bonded to each other via any one of a single bond, and a methylene group and an ethylene group each of which may have an alkyl group to form a ring structure;

$Ar_3$ represents a fused polycyclic aromatic hydrocarbon group formed by fusion of 4 or 5 six-membered rings, excluding an acene group and a 2,7-pyrene group, $Ar_3$ may further have a fluorine atom, a cyano group, a methyl group, or a tert-butyl group, and when $Ar_2$ represents an aromatic hydrocarbon group having 6 to 18 carbon atoms or a heteroaromatic ring group having 3 to 15 carbon atoms, $Ar_2$ and $Ar_3$ may be bonded to each other via any one of a single bond, and a methylene group and an ethylene group each of which may have an alkyl group to form a ring structure; and Q represents a substituent selected from a group of substituents represented by general formulae [2a] to [2e]:

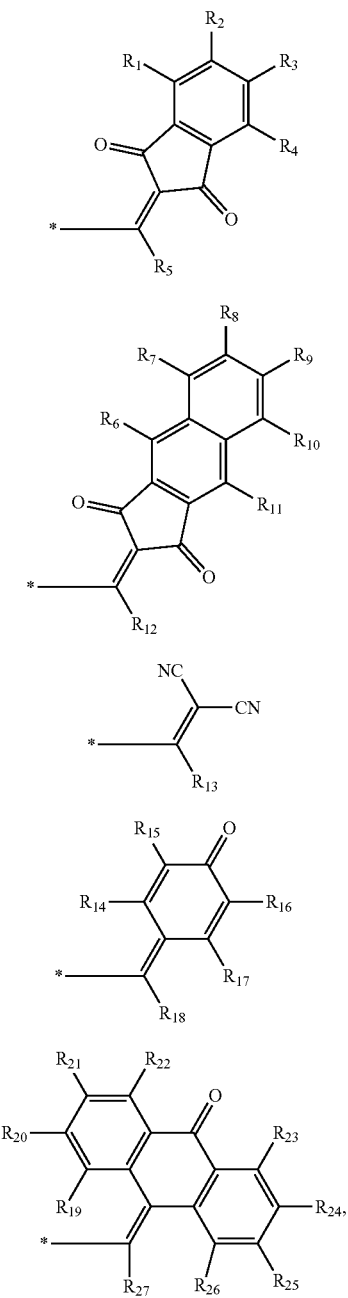

wherein, in the formulae [2a] to [2e], $R_1$ to $R_{27}$ each represents a substituent selected from a hydrogen atom, a fluorine atom, an alkyl group having 1 to 4 carbon atoms, or a cyano group, and * represents a bonding site with $Ar_3$.

12. The imaging element according to claim 11, further comprising one of a color filter and an optical filter, which corresponds to the light-receiving pixel.

13. The imaging element according to claim 12, wherein the imaging element comprises the optical filter, and the optical filter comprises any one of a low-pass filter configured to transmit light having a wavelength equal to or longer than an infrared wavelength and a long-pass filter configured to transmit light having a wavelength equal to or shorter than an ultraviolet wavelength.

14. The imaging element according to claim 11, further comprising an optical member, which is arranged so as to correspond to each of a plurality of the light-receiving pixels.

15. An imaging apparatus comprising:
an imaging optical system; and
an imaging element configured to receive light that has passed the imaging optical system,
wherein the imaging element comprises the imaging element of claim 11.

16. An imaging apparatus comprising:
a joining portion capable of being joined to an imaging optical system; and
the imaging element of claim 11.

17. The imaging apparatus according to claim 15, wherein the imaging apparatus comprises one of a digital camera and a digital still camera.

18. The imaging apparatus according to claim 15, further comprising a receiving unit configured to receive a signal from an outside, wherein the signal comprises a signal configured to control at least one of an imaging range of the imaging apparatus, a start of imaging thereof, and an end of the imaging.

19. The imaging apparatus according to claim 15, further comprising a transmitting unit configured to transmit an acquired image to an outside.

20. An organic compound represented any one of formulae A1, A2, A5, A8, A9, A13, A14, A16, and A19-A24:

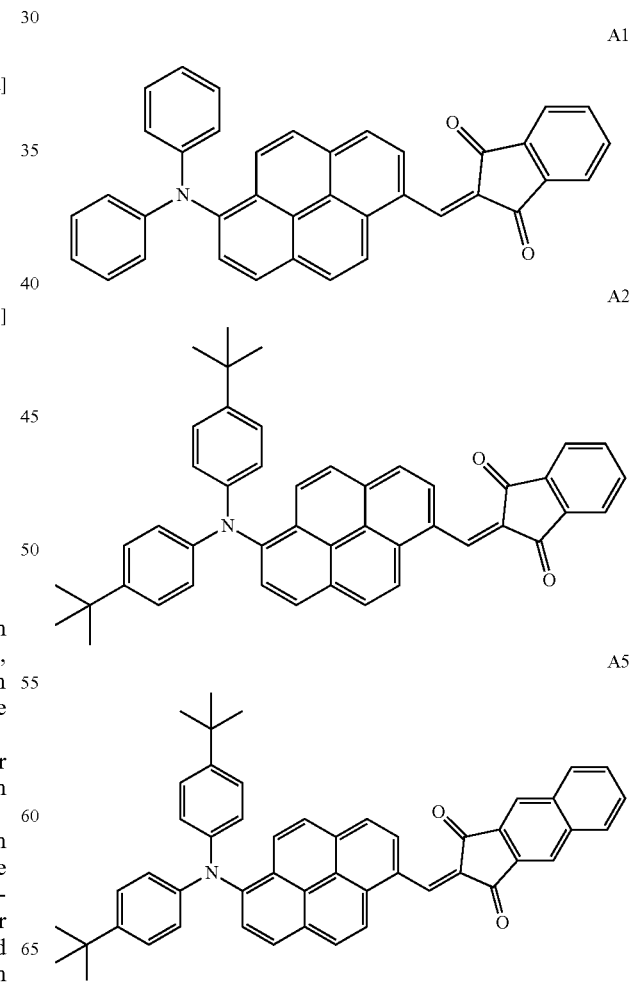

A8
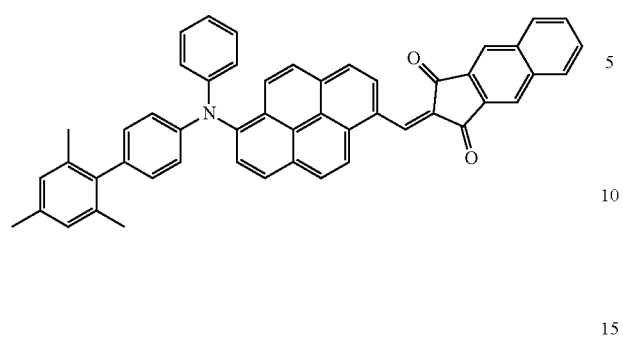
A16
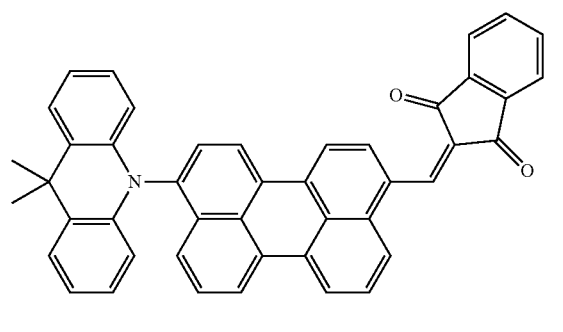
A9
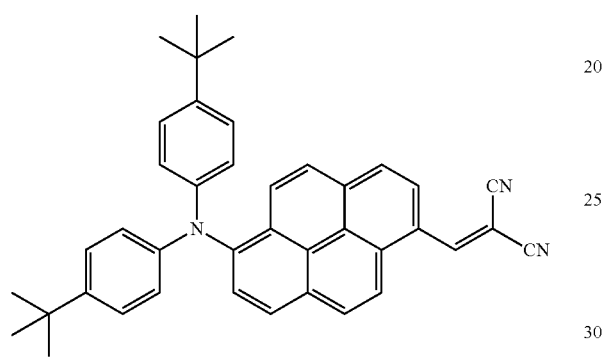
A19
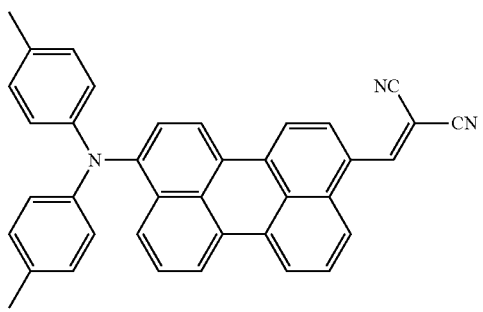 [SMILES: Cc1ccc(N(c2ccc(C)cc2)c2ccc3c4ccc(C=C(C#N)C#N)c5cccc(c6cccc2c63)c54)cc1]
A13
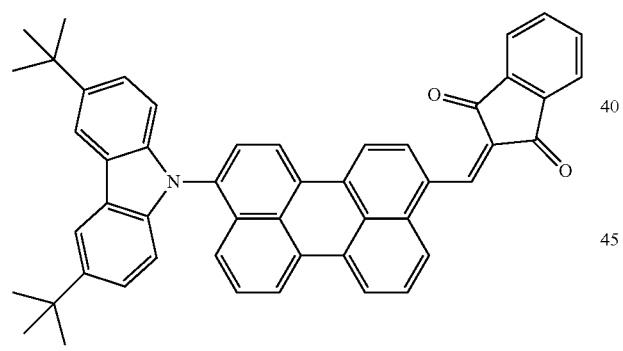
A20
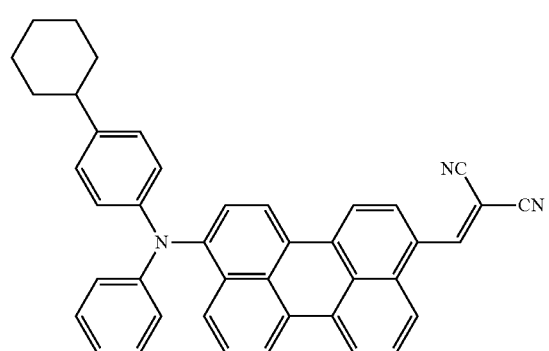
A14
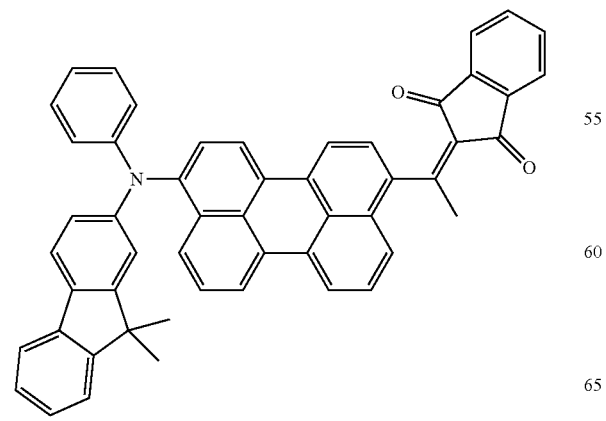
A21
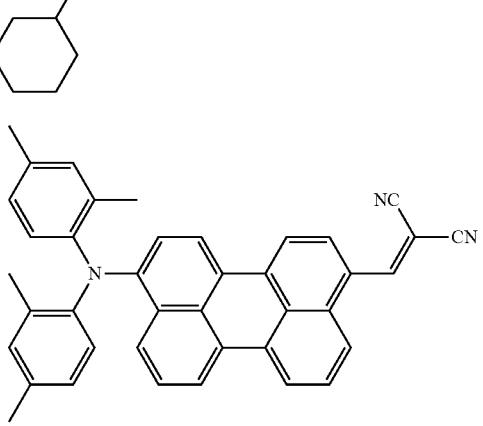

A22
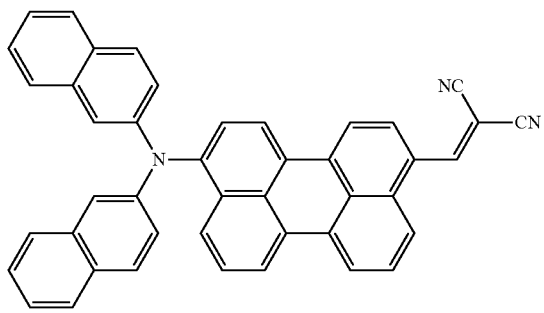
A23
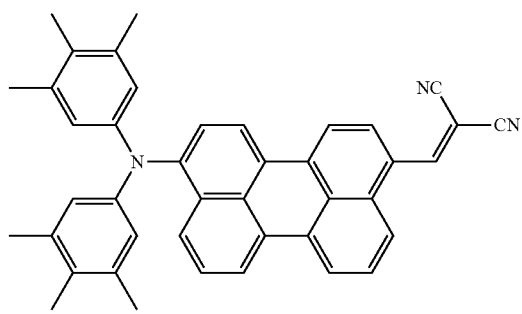
A24
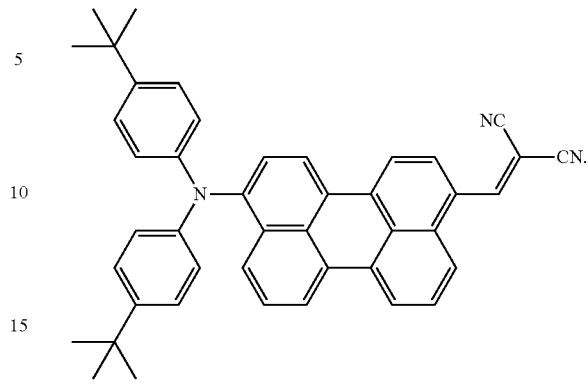
21. An organic photoelectric conversion element comprising:
   anode;
   cathode; and
   a photoelectric converter, which is arranged between the anode and the cathode,
   wherein the photoelectric converter includes at least a first organic compound layer, and
   wherein the first organic compound layer contains the organic compound according to claim 20.
* * * * *